United States Patent
Schaeffer

(10) Patent No.: US 10,166,017 B2
(45) Date of Patent: Jan. 1, 2019

(54) MEDICAL DEVICES HAVING A RELEASABLE TUBULAR MEMBER AND METHODS OF USING THE SAME

(71) Applicant: Cook Medical Technologies LLC, Bloomington, IN (US)

(72) Inventor: Darin Schaeffer, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 488 days.

(21) Appl. No.: 14/420,780

(22) PCT Filed: Aug. 4, 2014

(86) PCT No.: PCT/US2014/049589
§ 371 (c)(1),
(2) Date: Feb. 10, 2015

(87) PCT Pub. No.: WO2015/020953
PCT Pub. Date: Feb. 12, 2015

(65) Prior Publication Data
US 2016/0007984 A1 Jan. 14, 2016

Related U.S. Application Data

(60) Provisional application No. 61/862,144, filed on Aug. 5, 2013.

(51) Int. Cl.
*A61B 1/32* (2006.01)
*A61B 17/02* (2006.01)
(Continued)

(52) U.S. Cl.
CPC .......... *A61B 17/0218* (2013.01); *A61B 17/34* (2013.01); *A61B 17/3415* (2013.01);
(Continued)

(58) Field of Classification Search
None
See application file for complete search history.

(56) References Cited

U.S. PATENT DOCUMENTS

| 3,663,965 A | 5/1972 | Lee, Jr. et al. |
| 3,818,511 A | 6/1974 | Goldberg et al. |

(Continued)

FOREIGN PATENT DOCUMENTS

| EP | 0577400 | 1/1994 |
| EP | 1159924 | 12/2001 |

(Continued)

OTHER PUBLICATIONS

File history of U.S. Appl. No. 08/883,220, now U.S. Pat. No. 5,988,171, as of Jun. 3, 2014. Filing date, Jun. 26, 1997. First Named Inventor, Ze'ev Sohn. Title, Methods and Devices for the Treatment of Airway Obstruction, Sleep Apnea and Snoring.

(Continued)

*Primary Examiner* — Sameh Boles
(74) *Attorney, Agent, or Firm* — Buchanan Van Tuinen LLC

(57) ABSTRACT

Medical devices that have a releasable intermediate member and tubular member are described. Methods of using medical devices that have a releasable intermediate member and tubular member are also described. An example of a medical device comprises an elongate member, an intermediate member, and a tubular member. Each of the intermediate member and tubular member is releasably disposed on the elongate member.

3 Claims, 6 Drawing Sheets

(51) Int. Cl.
*A61B 17/34* (2006.01)
*A61B 17/00* (2006.01)

(52) U.S. Cl.
CPC ...... *A61B 17/3417* (2013.01); *A61B 17/3421* (2013.01); *A61B 2017/00477* (2013.01); *A61B 2017/345* (2013.01); *A61B 2017/3488* (2013.01); *A61B 2017/3492* (2013.01)

(56) References Cited

U.S. PATENT DOCUMENTS

| | | | |
|---|---|---|---|
| 4,024,859 A | 5/1977 | Slepyan et al. |
| 4,064,873 A | 12/1977 | Swenson |
| 4,217,664 A | 8/1980 | Faso |
| 4,338,937 A | 7/1982 | Lerman |
| 4,449,974 A | 5/1984 | Messingschlager |
| 4,608,972 A | 9/1986 | Small |
| 4,623,348 A | 11/1986 | Feit |
| 4,753,656 A | 6/1988 | Tofield et al. |
| 4,917,604 A | 4/1990 | Small |
| 5,084,064 A | 1/1992 | Barak et al. |
| 5,117,839 A | 6/1992 | Dance |
| 5,176,649 A | 1/1993 | Wakabayashi |
| 5,304,142 A | 4/1994 | Liebl et al. |
| 5,308,318 A | 5/1994 | Plassche, Jr. |
| 5,389,088 A | 2/1995 | Hageman |
| 5,425,761 A | 6/1995 | Lundgren |
| 5,477,860 A | 12/1995 | Essen-Moller |
| 5,489,278 A | 2/1996 | Abrahamson |
| 5,674,191 A | 10/1997 | Edwards et al. |
| 5,715,840 A | 2/1998 | Hall |
| 5,782,807 A | 7/1998 | Falvai et al. |
| 5,830,195 A | 11/1998 | Peters et al. |
| 5,951,518 A | 9/1999 | Licata et al. |
| 5,954,050 A | 9/1999 | Christopher |
| 5,974,724 A | 9/1999 | Frantz et al. |
| 5,988,171 A | 11/1999 | Sohn et al. |
| 6,159,158 A | 12/2000 | Lowe |
| 6,159,179 A | 12/2000 | Simonson |
| 6,159,208 A | 12/2000 | Hovda et al. |
| 6,397,841 B1 | 6/2002 | Kenyon et al. |
| 6,408,851 B1 | 6/2002 | Karell |
| 6,505,625 B1 | 1/2003 | Uenishi |
| 6,513,530 B2 | 2/2003 | Knudson et al. |
| 6,513,531 B2 | 2/2003 | Knudson et al. |
| 6,523,541 B2 | 2/2003 | Knudson et al. |
| 6,527,737 B2 | 3/2003 | Kaneshige |
| 6,536,424 B2 | 3/2003 | Fitton |
| 6,536,439 B1 | 3/2003 | Palmisano |
| 6,585,703 B1 | 7/2003 | Kassel et al. |
| 6,619,290 B1 | 9/2003 | Zacco |
| 6,764,464 B2 | 7/2004 | McGuckin, Jr. et al. |
| 6,895,963 B1 | 5/2005 | Martin et al. |
| 6,910,483 B2 | 6/2005 | Daly et al. |
| 6,955,172 B2 | 10/2005 | Nelson et al. |
| 6,966,319 B2 | 11/2005 | Fitton |
| 6,974,419 B1 | 12/2005 | Voss et al. |
| 7,004,172 B1 | 2/2006 | Zacco |
| 7,004,941 B2 | 2/2006 | Tvinnereim et al. |
| 7,037,290 B2 | 5/2006 | Gardeski et al. |
| 7,047,979 B2 | 5/2006 | Conrad et al. |
| 7,063,089 B2 | 6/2006 | Knudson et al. |
| 7,073,505 B2 | 7/2006 | Nelson et al. |
| 7,090,672 B2 | 8/2006 | Underwood et al. |
| 7,128,069 B2 | 10/2006 | Farrugia et al. |
| 7,168,429 B2 | 1/2007 | Matthews et al. |
| 7,188,627 B2 | 3/2007 | Nelson et al. |
| 7,195,646 B2 | 3/2007 | Nahleili |
| 7,213,599 B2 | 5/2007 | Conrad et al. |
| 7,216,647 B2 | 5/2007 | Lang et al. |
| 7,232,462 B2 | 6/2007 | Schaeffer |
| 7,255,109 B2 | 8/2007 | Knudson et al. |
| 7,269,453 B2 | 9/2007 | Mogul |
| 7,291,112 B2 | 11/2007 | Martin et al. |
| 7,337,778 B2 | 3/2008 | Martin et al. |
| 7,337,781 B2 | 3/2008 | Vassallo |
| 7,360,542 B2 | 4/2008 | Nelson et al. |
| 7,363,926 B2 | 4/2008 | Pflueger et al. |
| 7,387,634 B2 | 6/2008 | Benderev |
| 7,401,611 B2 | 7/2008 | Conrad et al. |
| 7,491,200 B2 | 2/2009 | Underwood |
| 7,507,258 B2 | 3/2009 | Nahleili |
| 7,607,439 B2 | 10/2009 | Li |
| 7,644,714 B2 | 1/2010 | Atkinson et al. |
| 7,658,192 B2 | 2/2010 | Harrington |
| 7,669,603 B2 | 3/2010 | Knudson et al. |
| 7,673,635 B2 | 3/2010 | Conrad et al. |
| 7,680,538 B2 | 3/2010 | Durand et al. |
| 7,703,460 B2 | 4/2010 | Conrad et al. |
| 7,731,708 B2 | 6/2010 | Haarala et al. |
| 7,762,991 B2 | 7/2010 | Bierman et al. |
| 7,766,926 B2 | 8/2010 | Bosley, Jr. et al. |
| 7,770,582 B2 | 8/2010 | Chen et al. |
| 7,789,843 B2 | 9/2010 | Ray |
| 7,793,661 B2 | 9/2010 | MacKen |
| 7,798,149 B2 | 9/2010 | Haduong |
| 7,810,502 B1 | 10/2010 | Nguyen et al. |
| 7,810,503 B2 | 10/2010 | Magnin |
| 7,813,812 B2 | 10/2010 | Kieval et al. |
| 7,819,122 B2 | 10/2010 | Abramson |
| 7,827,038 B2 | 11/2010 | Richard et al. |
| 7,827,988 B2 | 11/2010 | Matthews et al. |
| 7,827,991 B2 | 11/2010 | Maher |
| 7,832,402 B2 | 11/2010 | Nelissen |
| 7,832,403 B2 | 11/2010 | Halstrom et al. |
| 7,836,888 B2 | 11/2010 | Hegde et al. |
| 7,836,889 B2 | 11/2010 | Kusukawa |
| 7,845,356 B2 | 12/2010 | Paraschac et al. |
| 7,845,357 B2 | 12/2010 | Buscemi et al. |
| 7,856,979 B2 | 12/2010 | Doshi et al. |
| 7,856,980 B2 | 12/2010 | Lang et al. |
| 7,861,722 B2 | 1/2011 | Keropian |
| 7,861,723 B2 | 1/2011 | Dedrick et al. |
| 7,861,724 B2 | 1/2011 | Keropian |
| 7,862,721 B2 | 1/2011 | Bergersen |
| 7,870,860 B2 | 1/2011 | McCormick et al. |
| 7,874,291 B2 | 1/2011 | Ging et al. |
| 7,874,294 B2 | 1/2011 | Burger |
| 7,884,101 B2 | 2/2011 | Teegarden et al. |
| 7,909,037 B2 | 3/2011 | Hegde et al. |
| 7,909,038 B2 | 3/2011 | Hegde et al. |
| 7,918,228 B2 | 4/2011 | Smernoff |
| 7,921,850 B2 | 4/2011 | Nelson et al. |
| 7,934,506 B2 | 5/2011 | Woodson et al. |
| 7,935,065 B2 | 5/2011 | Martin et al. |
| 7,938,114 B2 | 5/2011 | Matthews et al. |
| 7,949,400 B2 | 5/2011 | Kieval et al. |
| 7,954,494 B1 | 6/2011 | Connor |
| 7,954,496 B2 | 6/2011 | Jansheski et al. |
| 7,955,267 B2 | 6/2011 | Voss et al. |
| 7,958,895 B2 | 6/2011 | Nelson et al. |
| 7,958,896 B2 | 6/2011 | Nelson et al. |
| 7,959,554 B2 | 6/2011 | McAlexander et al. |
| 7,971,591 B2 | 7/2011 | Jansheski |
| 7,975,700 B2 | 7/2011 | Frazier et al. |
| 7,975,701 B2 | 7/2011 | Bergersen |
| 7,976,471 B2 | 7/2011 | Martin et al. |
| 7,980,248 B2 | 7/2011 | Hegde et al. |
| 7,984,714 B2 | 7/2011 | Hausmann et al. |
| 7,987,854 B2 | 8/2011 | Arni |
| 7,992,564 B2 | 8/2011 | Doshi et al. |
| 7,992,566 B2 | 8/2011 | Pflueger et al. |
| 7,992,567 B2 | 8/2011 | Hirotsuka et al. |
| 7,997,266 B2 | 8/2011 | Frazier et al. |
| 7,997,267 B2 | 8/2011 | Ging et al. |
| 7,997,276 B2 | 8/2011 | Goff |
| 8,001,971 B2 | 8/2011 | Boucher et al. |
| 8,001,972 B2 | 8/2011 | Eubank |
| 8,001,973 B2 | 8/2011 | Sotos et al. |
| 8,015,975 B2 | 9/2011 | Zohlmann, Jr. |
| 8,020,560 B2 | 9/2011 | Paraschac et al. |
| 8,025,063 B2 | 9/2011 | Sotos et al. |
| 8,026,405 B2 | 9/2011 | Beaudry |
| 8,028,703 B1 | 10/2011 | Moses |

(56) References Cited

U.S. PATENT DOCUMENTS

| | | |
|---|---|---|
| 8,033,282 B2 | 10/2011 | Eubank |
| 8,037,885 B2 | 10/2011 | Metzger et al. |
| 8,037,886 B2 | 10/2011 | Sotos et al. |
| 8,047,201 B2 | 11/2011 | Guyuron et al. |
| 8,047,206 B2 | 11/2011 | Boucher et al. |
| 8,052,646 B2 | 11/2011 | Schweikert et al. |
| 8,070,693 B2 | 12/2011 | Ayala et al. |
| 8,074,655 B2 | 12/2011 | Sanders |
| 8,096,303 B2 | 1/2012 | Dineen et al. |
| 8,147,456 B2 | 4/2012 | Fisher et al. |
| 8,167,787 B2 | 5/2012 | Gillis |
| 8,220,466 B2 | 7/2012 | Frazier et al. |
| 8,220,467 B2 | 7/2012 | Sanders |
| 8,327,854 B2 | 12/2012 | Gillis et al. |
| 8,414,537 B2 | 4/2013 | Nardeo et al. |
| 8,425,466 B2 | 4/2013 | Sargent, Jr. |
| 8,460,322 B2 | 6/2013 | van der Burg et al. |
| 8,529,544 B2 | 9/2013 | Haarala et al. |
| 8,535,310 B2 | 9/2013 | Hardin, Jr. et al. |
| 8,535,349 B2 | 9/2013 | Chen et al. |
| 8,603,185 B2 | 12/2013 | Shah et al. |
| 9,216,015 B2 * | 12/2015 | Wilson ............... A61B 17/3431 |
| 9,603,673 B2 * | 3/2017 | Nino ............. A61B 17/320016 |
| 2001/0050085 A1 | 12/2001 | Knudson et al. |
| 2003/0111079 A1 | 6/2003 | Matthews et al. |
| 2003/0140925 A1 | 7/2003 | Sapienza et al. |
| 2003/0168064 A1 | 9/2003 | Daly et al. |
| 2004/0028676 A1 | 2/2004 | Klein et al. |
| 2004/0073272 A1 | 4/2004 | Knudson et al. |
| 2004/0099275 A1 | 5/2004 | Zacco |
| 2004/0112387 A1 | 6/2004 | Lang et al. |
| 2004/0153127 A1 | 8/2004 | Gordon et al. |
| 2004/0187870 A1 | 9/2004 | Matthews et al. |
| 2005/0005937 A1 | 1/2005 | Farrugia et al. |
| 2005/0098184 A1 | 5/2005 | Conrad et al. |
| 2005/0103339 A1 | 5/2005 | Daly et al. |
| 2005/0126563 A1 | 6/2005 | van der Burg et al. |
| 2005/0217673 A1 | 10/2005 | Daly et al. |
| 2005/0256452 A1 | 11/2005 | DeMarchi et al. |
| 2005/0267547 A1 | 12/2005 | Knudson et al. |
| 2005/0268914 A1 | 12/2005 | Paoluccio et al. |
| 2005/0279365 A1 | 12/2005 | Armijo et al. |
| 2006/0000475 A1 | 1/2006 | Matthews et al. |
| 2006/0070626 A1 | 4/2006 | Frazier et al. |
| 2006/0112962 A1 | 6/2006 | Tebbutt et al. |
| 2006/0150986 A1 | 7/2006 | Roue et al. |
| 2006/0169289 A1 | 8/2006 | Zacco |
| 2006/0201519 A1 | 9/2006 | Frazier et al. |
| 2006/0201520 A1 | 9/2006 | Christensen, III |
| 2006/0207606 A1 | 9/2006 | Roue et al. |
| 2006/0207607 A1 | 9/2006 | Hirotsuka et al. |
| 2006/0207608 A1 | 9/2006 | Hirotsuka et al. |
| 2006/0207612 A1 | 9/2006 | Jackson et al. |
| 2006/0235264 A1 | 10/2006 | Vassallo |
| 2006/0235877 A1 | 10/2006 | Richard et al. |
| 2006/0263145 A1 | 11/2006 | Pal et al. |
| 2007/0016166 A1 | 1/2007 | Thistle |
| 2007/0132117 A1 | 6/2007 | Truitt et al. |
| 2007/0134085 A1 | 6/2007 | Daly et al. |
| 2007/0144539 A1 | 6/2007 | van der Burg et al. |
| 2007/0157928 A1 | 7/2007 | Pujol et al. |
| 2007/0157934 A1 | 7/2007 | Lang et al. |
| 2007/0207994 A1 | 9/2007 | Teegarden et al. |
| 2007/0209664 A1 | 9/2007 | Paraschac et al. |
| 2007/0209665 A1 | 9/2007 | Gillis et al. |
| 2007/0244086 A1 | 10/2007 | Teegarden et al. |
| 2007/0256693 A1 | 11/2007 | Paraschac et al. |
| 2007/0287923 A1 | 12/2007 | Adkins et al. |
| 2008/0023012 A1 | 1/2008 | Dineen et al. |
| 2008/0027480 A1 | 1/2008 | van der Burg et al. |
| 2008/0027560 A1 | 1/2008 | Jackson et al. |
| 2008/0035160 A1 | 2/2008 | Woodson et al. |
| 2008/0041382 A1 | 2/2008 | Matthews et al. |
| 2008/0041383 A1 | 2/2008 | Matthews et al. |
| 2008/0041398 A1 | 2/2008 | Hegde et al. |
| 2008/0045813 A1 | 2/2008 | Phuah et al. |
| 2008/0053461 A1 | 3/2008 | Hirotsuka et al. |
| 2008/0058584 A1 | 3/2008 | Hirotsuka et al. |
| 2008/0066753 A1 | 3/2008 | Martin et al. |
| 2008/0066765 A1 | 3/2008 | Paraschac et al. |
| 2008/0066769 A1 | 3/2008 | Dineen et al. |
| 2008/0097380 A1 | 4/2008 | Li |
| 2008/0099019 A1 | 5/2008 | Martin et al. |
| 2008/0115791 A1 | 5/2008 | Heine |
| 2008/0194953 A1 | 8/2008 | Kerber |
| 2008/0208265 A1 | 8/2008 | Frazier et al. |
| 2008/0251071 A1 | 10/2008 | Armitstead et al. |
| 2008/0306442 A1 | 12/2008 | Bardsley et al. |
| 2009/0044814 A1 | 2/2009 | Iancea et al. |
| 2009/0053306 A1 | 2/2009 | Agarwal et al. |
| 2009/0060905 A1 | 3/2009 | Martin et al. |
| 2009/0088599 A1 | 4/2009 | Zook et al. |
| 2009/0099471 A1 | 4/2009 | Broadley et al. |
| 2009/0131923 A1 | 5/2009 | Connors et al. |
| 2010/0004264 A1 | 1/2010 | Xiong et al. |
| 2010/0010061 A1 | 1/2010 | Cooper et al. |
| 2010/0016694 A1 | 1/2010 | Martin et al. |
| 2010/0028026 A1 | 2/2010 | Inami et al. |
| 2010/0106246 A1 | 4/2010 | Rousseau et al. |
| 2010/0108066 A1 | 5/2010 | Martin et al. |
| 2010/0108077 A1 | 5/2010 | Lindh et al. |
| 2010/0132719 A1 | 6/2010 | Jacobs et al. |
| 2010/0144701 A1 | 6/2010 | Cooper et al. |
| 2010/0234946 A1 | 9/2010 | Rousseau |
| 2010/0286793 A1 | 11/2010 | Newman et al. |
| 2010/0300458 A1 | 12/2010 | Stubbs et al. |
| 2011/0005526 A1 | 1/2011 | Garabadian et al. |
| 2011/0005529 A1 | 1/2011 | Doshi et al. |
| 2011/0005530 A1 | 1/2011 | Doshi et al. |
| 2011/0017220 A1 | 1/2011 | Lindsay et al. |
| 2011/0030700 A1 | 2/2011 | Wilson |
| 2011/0030701 A1 | 2/2011 | Lang et al. |
| 2011/0036357 A1 | 2/2011 | Abramson |
| 2011/0046712 A1 | 2/2011 | Melsheimer et al. |
| 2011/0048430 A1 | 3/2011 | Arnon |
| 2011/0048431 A1 | 3/2011 | Li |
| 2011/0056498 A1 | 3/2011 | Lang et al. |
| 2011/0067708 A1 | 3/2011 | Doshi et al. |
| 2011/0067709 A1 | 3/2011 | Doshi et al. |
| 2011/0073119 A1 | 3/2011 | Chen et al. |
| 2011/0088701 A1 | 4/2011 | Thornton |
| 2011/0092910 A1 | 4/2011 | Schultz |
| 2011/0094520 A1 | 4/2011 | Mikhailenok et al. |
| 2011/0100376 A1 | 5/2011 | Rousseau |
| 2011/0100378 A1 | 5/2011 | Rousseau |
| 2011/0108041 A1 | 5/2011 | Sather et al. |
| 2011/0114099 A1 | 5/2011 | Goldstein |
| 2011/0120476 A1 | 5/2011 | Keropian |
| 2011/0130249 A1 | 6/2011 | Mikhailenok et al. |
| 2011/0132378 A1 | 6/2011 | Levendowski et al. |
| 2011/0155142 A1 | 6/2011 | Boucher et al. |
| 2011/0155143 A1 | 6/2011 | Shantha |
| 2011/0155144 A1 | 6/2011 | Toussaint |
| 2011/0162658 A1 | 7/2011 | Fisher et al. |
| 2011/0166673 A1 | 7/2011 | Patel et al. |
| 2011/0168186 A1 | 7/2011 | Halstrom |
| 2011/0168187 A1 | 7/2011 | Nelissen |
| 2011/0168188 A1 | 7/2011 | Moore et al. |
| 2011/0174315 A1 | 7/2011 | Zhang et al. |
| 2011/0178439 A1 | 7/2011 | Irwin et al. |
| 2011/0180075 A1 | 7/2011 | Chen et al. |
| 2011/0180076 A1 | 7/2011 | Hegde et al. |
| 2011/0183928 A1 | 7/2011 | Thede et al. |
| 2011/0192404 A1 | 8/2011 | Chen |
| 2011/0203598 A1 | 8/2011 | Favet et al. |
| 2011/0214678 A1 | 9/2011 | Zhang et al. |
| 2011/0218451 A1 | 9/2011 | Lai et al. |
| 2011/0220123 A1 | 9/2011 | Robson |
| 2011/0220124 A1 | 9/2011 | Vaska et al. |
| 2011/0220125 A1 | 9/2011 | Van Dyke et al. |
| 2011/0226261 A1 | 9/2011 | Hernandez |
| 2011/0226262 A1 | 9/2011 | Gillis et al. |
| 2011/0226263 A1 | 9/2011 | Gillis et al. |
| 2011/0226264 A1 | 9/2011 | Friedman et al. |

(56) References Cited

U.S. PATENT DOCUMENTS

| | | |
|---|---|---|
| 2011/0232651 A1 | 9/2011 | Diers |
| 2011/0232652 A1 | 9/2011 | Levendowski et al. |
| 2011/0240037 A1 | 10/2011 | Hegde et al. |
| 2011/0240038 A1 | 10/2011 | Doshi et al. |
| 2011/0245850 A1 | 10/2011 | van der Burg et al. |
| 2011/0259345 A1 | 10/2011 | Cullen |
| 2011/0259346 A1 | 10/2011 | Tsuiki et al. |
| 2011/0265801 A1 | 11/2011 | Cullen |
| 2011/0265802 A1 | 11/2011 | Ha |
| 2011/0308530 A1 | 12/2011 | Gillis et al. |
| 2012/0162401 A1 | 6/2012 | Melder et al. |
| 2012/0226341 A1 | 9/2012 | Schreck et al. |
| 2012/0265055 A1 | 10/2012 | Melsheimer et al. |
| 2013/0041314 A1 | 2/2013 | Dillon |
| 2013/0046138 A1 | 2/2013 | McLawhorn |
| 2013/0056009 A1 | 3/2013 | Mohan et al. |
| 2013/0060267 A1 | 3/2013 | Farnan et al. |
| 2013/0085546 A1 | 4/2013 | Bolea et al. |
| 2013/0123705 A1 | 5/2013 | Holm et al. |
| 2013/0180528 A1 | 7/2013 | Zhou et al. |
| 2013/0213409 A1 | 8/2013 | Podmore et al. |
| 2013/0226146 A1 | 8/2013 | Tekulve |
| 2013/0237967 A1 | 9/2013 | Schaeffer et al. |
| 2013/0237968 A1 | 9/2013 | Schaeffer et al. |
| 2013/0238003 A1 | 9/2013 | Fischer et al. |
| 2013/0245662 A1 | 9/2013 | Schaeffer et al. |
| 2014/0102460 A1 | 4/2014 | Catalano |
| 2014/0114290 A1 | 4/2014 | Okamura |

FOREIGN PATENT DOCUMENTS

| | | |
|---|---|---|
| EP | 1501447 | 3/2009 |
| JP | H03-070150 | 7/1991 |
| JP | H10-201851 | 1/1997 |
| JP | 2001-527425 | 12/2001 |
| JP | 2001527425 | 12/2001 |
| JP | 2004-248773 | 9/2004 |
| JP | 2007-082989 | 4/2007 |
| JP | 2007-209721 | 8/2007 |
| JP | 2009-521992 | 6/2009 |
| WO | WO1993000947 | 1/1993 |
| WO | WO199734649 | 9/1997 |
| WO | WO199850093 | 11/1998 |
| WO | WO2003075794 | 9/2003 |
| WO | WO2005056079 | 6/2005 |
| WO | WO2007056583 | 5/2007 |
| WO | WO2007149469 | 12/2007 |
| WO | WO2009140197 | 11/2009 |
| WO | WO2010045546 | 4/2010 |
| WO | WO2010051195 | 5/2010 |
| WO | WO2011068952 | 6/2011 |
| WO | WO2011123714 | 10/2011 |
| WO | WO2013002286 | 1/2013 |
| WO | WO2013010169 | 1/2013 |
| WO | WO2014189540 | 11/2014 |
| WO | WO2015020953 | 2/2015 |

OTHER PUBLICATIONS

File history of U.S. Appl. No. 10/877,003, now U.S. Pat. No. 7,213,599, as of Jun. 3, 2014. Filing date, Jun. 24, 2004. First Named Inventor, Timothy R. Conrad. Title, Airway Implant.

File history of U.S. Appl. No. 11/757,501, now U.S. Pat. No. 7,703,460, as of Jun. 3, 2014. Filing date, Jun. 4, 2007. First Named Inventor, Timothy R. Conrad. Title, Tongue Implant.

File history of U.S. Appl. No. 12/214,084 as of Jun. 3, 2014. Filing date, Jun. 17, 2008. First Named Inventor, Octavian Iancea. Title, Implantable devices, systems, and methods for maintaining desired orientations in targeted tissue regions.

Woodson et al,"Multicenter study of a novel adjustable tongue-advancement device for obstructive sleep apnea," Otolaryngology and Head and Neck Surgery, Jun. 10, 2010, pp. 585-590, 143(4), Sage Publications.

Woodson et al, "Response to: Multicenter study of a novel adjustable tongue-advancement device for obstructive sleep apnea," Otolaryngology and Head and Neck Surgery, 211, pp. 1009-1010, 144(6), Sage Publications.

Hamans et al, "A novel tongue implant for tongue advancement for obstructive sleep apnea: Feasibility, safety and histology in a canine model," Journal of Musculoskeletal and Neuronal Interactions, Dec. 29, 2009, pp. 100-111, 10(1), Hylonome.

Kezirian, Eric J., M.D.,M.P.H., "Drug-Induced Sleepy Endoscopy," Dr. Kezirian's Blog, pp. 1-3, http://www.sleep-doctor.com/surgical-treatment-overview/drug-induced-sleep-endoscopy/, 2009-2014.

Medical News Today, "Aspire Medical Announces First Implant in US and Start of Clinical Trial to Treat Sleep Apnea," www.medicalnewstoday.com, May 23, 2007.

Park, Dr. Steven Y., "Aspire Medical Advance System for obstructive sleep apnea," Dr. Park: Breathe better, sleep better, live better. pp. 1-4. Oct. 6, 2010. <http://doctorstevenpark.com/aspire-medical-advance-system-for-obstructive-sleep-apnea>.

PR Newswire, "Aspire Medical appoints Roseanne Varner as president and CEO [press release]," pp. 1-2. May 1, 2011. <http://www.prnewswire.com/news-releases/aspire-medical-appoints-roseanne-varner-as-president-and-ceo-57760852.html>.

Siesta Medical, "Siesta Medical Receives 510(k) Clearance for Encore System to treat Obstructive Sleep Apnea," Siesta Medical, Los Gatos, CA, Sep. 12, 2011.

Revent Medical, "The Revent Solution: Tongue Implanter Kit," 2014. pp. 1-2, Retrieved Aug. 12, 2014. <http://www.reventmedical.com/solution/>.

Revent Medical, "The Revent Solution: Implant," 2014. pp. 1-2, Retrieved Aug. 12, 2014. <www.reventmedical.com/solution/>.

Knobbe, Martens, Olson & Bear, LLP, "Amendment and response to non-Final Office Action dated Jan. 18, 2013, for U.S. Appl. No. 13/077,813," dated Mar. 31, 2011, First Named Inventor, van der Burg. Title, Suture Passer Systems and Methods for Tongue or Other Tissue Suspension and Compression.

Synmed, "E.G. Scan: Trans-nasal, disposable system for upper GI screening," SynMed Ltd., p. 1, United Kingdom.

Mizayahi, Soichiro, M.D., et al., "A trial study of RhinoSleep for the diagnosis of sleep apnea," Psychiatry and Clinical Neuroscience, 55, pp. 249-250, 2001.

International Searching Authority, International Search Report and Written Opinion for International application No. PCT/US2014/049341, dated Nov. 19, 2014, pp. 1-11.

Bosmed, "Laryngeal and Esophageal Products," Bosmed.com, accessed Oct. 1, 2012, p. 1.

Hood Laboratories, "Schaitkin Salivary Duct Cannula," HoodLabs.com, accessed Jan. 19, 2014, pp. 1-2.

Nahlieli, Oded, Et. Al., "Diagnosis and treatment of strictures and kinks in salivary gland ducts," J. Oral and Maxillofacial Surgery, vol. 59, Issue 5, pp. 484-490, May 2001.

International Searching Authority, "IPER," for Int. App. No. PCT/US2014/049589, dated Feb. 18, 2016, pp. 1-13.

State Intellectual Property Office of P.R. China, Notification of First Office Action, dated Oct. 9, 2017, p. 1-7 (English translation).

International Searching Authority, International Search Report and Written Opinion for International application No. PCT/US2015/032577, dated Aug. 5, 2015, pp. 1-10.

Japanese Patent Office, Office Action for Japanese application No. 2016-533359, dated Dec. 19, 2017, pp. 1-4.

Australian Government—IP Australia, "Examination report No. 1 for standard patent application," for Application No. 2014306232, dated Apr. 17, 2018; pp. 1-5.

State Intellectual Property Office Of P.R. China. "Notification of Second Office Action," p. 1-7, dated Jun. 20, 2018.

State Intellectual Property Office Of P.R. China. "Notification of Second Office Action," p. 1-6, English Translation, dated Jun. 20, 2018.

PCT Publication Application WO199300947, published Jan. 21, 1993, submitted as English translation for JP2001527425.

* cited by examiner

MEDICAL DEVICES HAVING A RELEASABLE TUBULAR MEMBER AND METHODS OF USING THE SAME

RELATED APPLICATION

This application claims the benefit of U.S. Provisional Application No. 61/862,144, filed on Aug. 5, 2013. The disclosure of this related application is hereby incorporated into this disclosure in its entirety.

FIELD

The disclosure relates generally to the field of medical devices. Particular embodiments are related to medical devices that have a releasable tubular member and methods of using a medical device that has a releasable tubular member.

BACKGROUND

A variety of medical devices have been developed to treat bodily passages, such as the salivary glands. For example, some medical devices have been developed that can be introduced into a bodily passage to provide access to the bodily passage during the performance of a procedure. However, a need exists for improved medical devices that can be introduced into a bodily passage and that can be used to provide access during treatment.

BRIEF SUMMARY OF SELECTED EXAMPLE EMBODIMENTS

A first example embodiment of a medical device comprises an elongate member, an intermediate member, and a tubular member. The elongate member has a proximal portion and a shaft that extends distally from the proximal portion. The proximal portion has a first outside diameter. The shaft has a first proximal end attached to the proximal portion and a first distal end. The shaft has a second outside diameter that is less than the first outside diameter. The intermediate member is releasably disposed on the shaft and has a second proximal end, a second distal end, an intermediate member body, and an outside diameter that is greater than the first outside diameter of the proximal portion. The intermediate member body defines a first intermediate member opening on the proximal end of the intermediate member, a second intermediate member opening on the distal end of the intermediate member, and an intermediate member lumen that extends from the first intermediate member opening to the second intermediate member opening. The intermediate member lumen has an inside diameter that is less than the first outside diameter of the proximal portion. The tubular member is releasably disposed on the shaft distal to the intermediate member and has a third proximal end, a third distal end, and a tubular member body. The tubular member body defines a first tubular member opening on the proximal end of the tubular member, a second tubular member opening on the distal end of the tubular member, and a tubular member lumen that extends from the first tubular member opening to the second tubular member opening.

A second example embodiment of a medical device comprises an elongate member, an intermediate member, and a tubular member. The elongate member has a proximal portion and a shaft that extends distally from the proximal portion. The proximal portion has a first outside diameter. The shaft has a first proximal end attached to the proximal portion, a tapered first distal end, and a length that extends from the first proximal end to the first distal end. The shaft has a second outside diameter that is less than the first outside diameter. The intermediate member is releasably disposed on the shaft and has a second proximal end, a second distal end, an intermediate member body, and an outside diameter that is greater than the first outside diameter of the proximal portion. The intermediate member body defines a first intermediate member opening on the proximal end of the intermediate member, a second intermediate member opening on the distal end of the intermediate member, and an intermediate member lumen that extends from the first intermediate member opening to the second intermediate member opening. The intermediate member lumen has an inside diameter that is less than the first outside diameter of the proximal portion. The tubular member is releasably disposed on the shaft distal to the intermediate member and has a third proximal end, a tapered third distal end, a length that extends from the third proximal end to the third distal end, and a tubular member body. The tubular member body defines a first tubular member opening on the proximal end of the tubular member, a second tubular member opening on the distal end of the tubular member, and a tubular member lumen that extends from the first tubular member opening to the second tubular member opening. The length of the tubular member is less than the length of the shaft. The third distal end of the tubular member is disposed proximal to the first distal end of the elongate member.

A third example embodiment of a medical device comprises an elongate member, an intermediate member, and a tubular member. The elongate member has a proximal portion and a shaft that extends distally from the proximal portion. The proximal portion has a first outside diameter. The shaft has a first proximal end attached to the proximal portion, a tapered first distal end, and a length that extends from the first proximal end to the first distal end. The shaft has a second outside diameter that is less than the first outside diameter. The intermediate member is releasably disposed on the shaft and has a second proximal end, a second distal end, an intermediate member body, and an outside diameter that is greater than the first outside diameter of the proximal portion. The intermediate member body defines a first intermediate member opening, a second intermediate member opening, an intermediate member lumen, a first surface, a second surface, a frustoconical protuberance, and a support post. The first intermediate member opening is defined on the proximal end of the intermediate member. The second intermediate member opening is defined on the distal end of the intermediate member. The intermediate member lumen extends from the first intermediate member opening to the second intermediate member opening. The intermediate member lumen has an inside diameter that is less than the first outside diameter of the proximal portion. The first surface is disposed on the second proximal end and is opposably facing the second surface. The frustoconical protuberance extends distally from the second surface and tapers from the second surface toward the second distal end. The support post extends distally from the frustoconical protuberance to a support post end. The tubular member is releasably disposed on the shaft distal to the intermediate member and has a third proximal end, a tapered third distal end, a length that extends from the third proximal end to the third distal end, a frustoconical proximal portion that tapers from the third proximal end toward the third distal end, and a tubular member body. The tubular member body defines a first tubular member opening on the proximal end of the tubular member, a second tubular member opening on the distal end of the tubular member, a tubular member lumen that extends from the first tubular member opening to the second tubular member opening, and a passageway that extends through the frustoconical proximal portion. The passageway provides access to the tubular member lumen. The tubular member lumen has a frustoconical proximal portion that tapers from the third proximal end toward the third distal end. The length of the tubular member is less than the length of the shaft. The third distal end of the tubular member is disposed proximal to the first distal end of the elongate member. The frustoconical protuberance is disposed within the frustoconical proximal portion of the tubular member lumen. The support post is disposed within the passageway defined by the tubular member body.

DETAILED DESCRIPTION

The following detailed description and the appended drawings describe and illustrate various example embodiments and example methods. The description and illustration of these examples are provided to enable one skilled in the art to make and use a medical device for the treatment of a bodily passage and/or practice a method of using a medical device to treat a bodily passage. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described. The use of "diameter" refers to the length of a straight line passing from side to side through the center of a body, element, or feature, and does not impart any structural configuration on the body, element, or feature. The term "cuboid," or variations thereof, does not require that each side of the element or component be square and only requires that the element or component have six surfaces, hypothetical or actual, at right angles to each other. The term "bodily passage" or "body passage" refers to any passage within the body of an animal, including, but not limited to, humans, and includes elongate passages. The term "salivary duct" refers to the parotid ducts, submandibular ducts, and/or sublingual ducts. The term "urinary tract" refers to the kidneys, renal pelvis, ureters, bladder, urethra, and/or any other portion of the urinary system. The term "medication" refers to any fluid, drug, agent, therapeutic agent, and/or any other material used to treat a patient.

Figure 1:
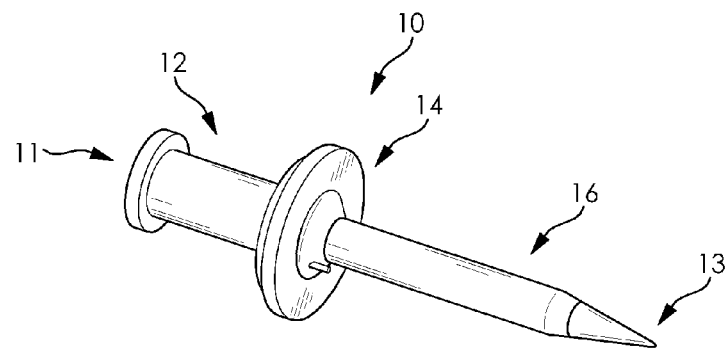
FIG. 1 illustrates a perspective view of an embodiment of a medical device.
Figure 2:
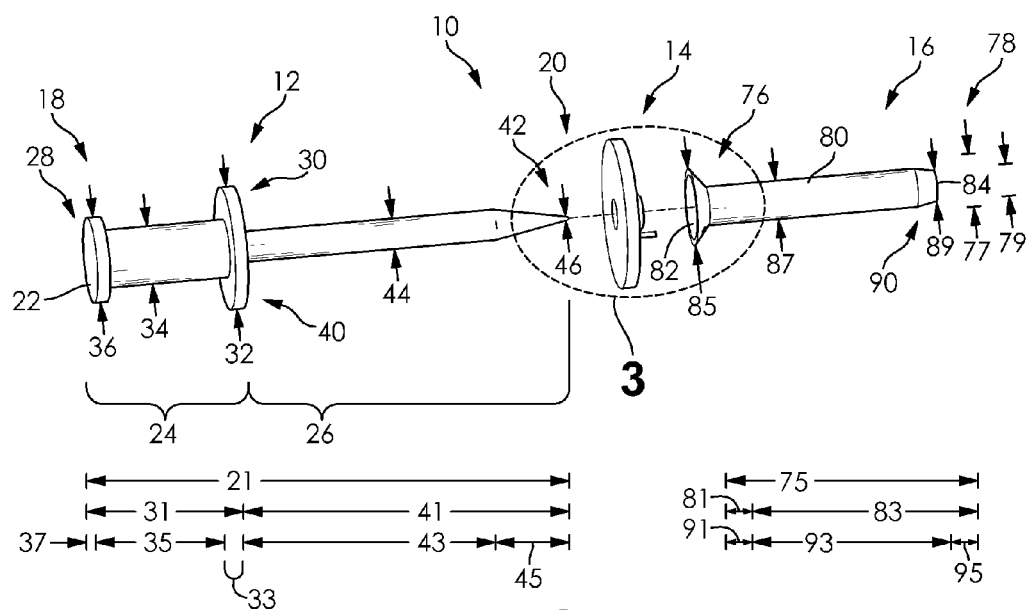
FIG. 2 is an exploded perspective view of the medical device illustrated in FIG. 1.
Figure 3:
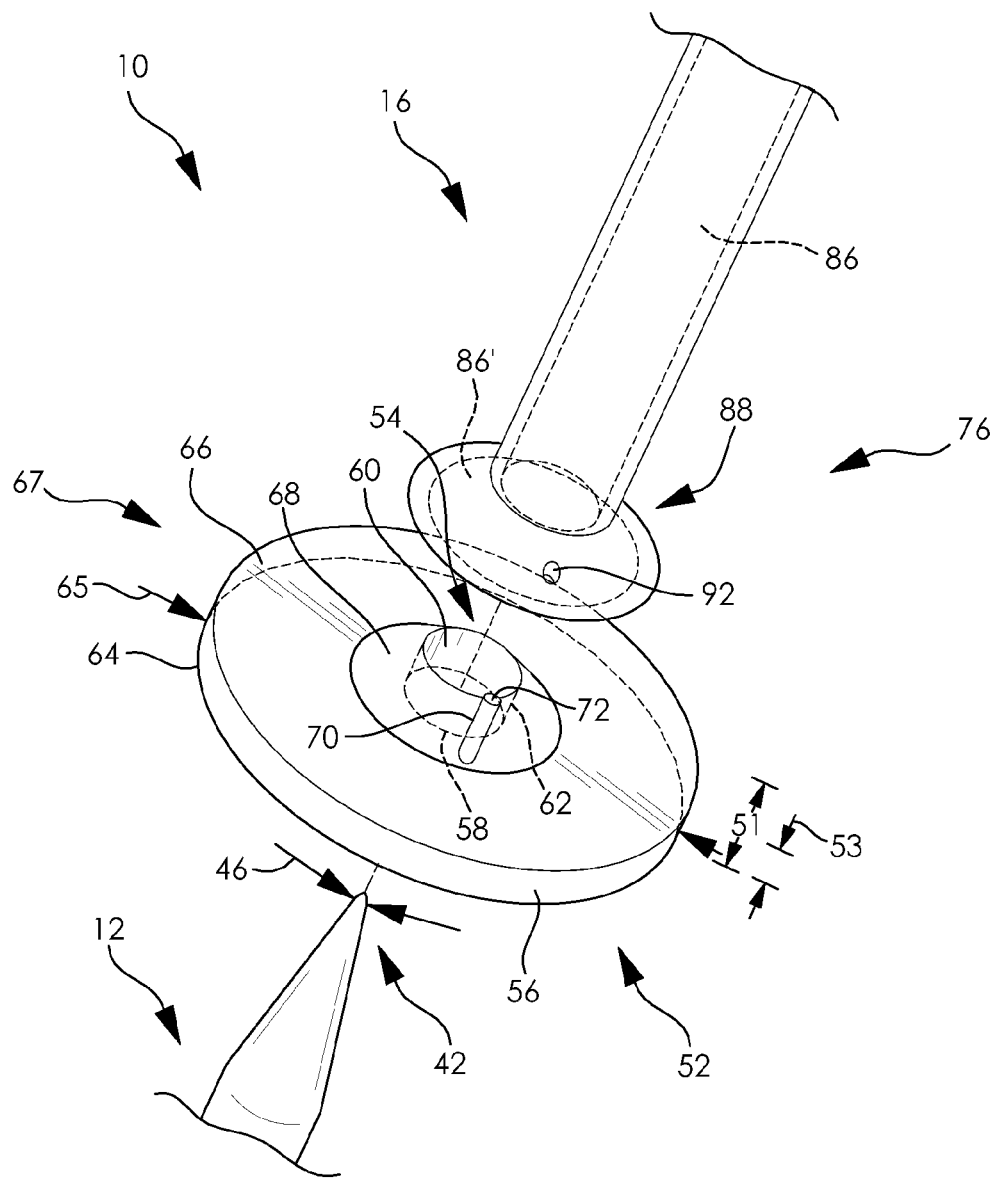
FIG. 3 is a magnified view of area 3 illustrated in FIG. 2.

FIGS. 1, 2, and 3 illustrate a medical device 10 that comprises an elongate member 12, an intermediate member 14, and a tubular member 16. Medical device 10 has a proximal end 11 and a distal end 13. Each of the intermediate member 14 and tubular member 16 are releasably disposed on the elongate member 12, as described in more detail herein.

In the illustrated embodiment, the elongate member 12 comprises a proximal end 18, a distal end 20, a length 21, and a body 22 that defines a proximal portion 24 and a shaft 26. The length 21 of the elongate member 12 extends from the proximal end 18 to the distal end 20 of the elongate member 12.

The proximal portion 24 has a proximal end 28, a distal end 30, a length 31, a first outside diameter 32, a second outside diameter 34, and a third outside diameter 36. The length 31 of the proximal portion 24 extends from the proximal end 28 to the distal end 30 of the proximal portion 24. The first outside diameter 32 is disposed at the distal end 30 of the proximal portion 24, the second outside diameter 34 is disposed between the proximal end 28 and the distal end 30 of the proximal portion 24, and the third outside diameter 36 is disposed on the proximal end 28 of the proximal portion 24. Each of the first diameter 32 and the third outside diameter 36 is greater than the second outside diameter 34. The body 22 of the elongate member 12 defines the first outside diameter 32 along a first portion 33 of the length 31 of the proximal portion 24, the second outside diameter 34 along a second portion 35 of the length 31 of the proximal portion 24, and the third outside diameter 36 along a third portion 37 of the length 31 of the proximal portion 24. The first portion 33 extends from the distal end 30 toward the proximal end 28 to the second portion 35 and has a length that is less than the length 31 of the proximal portion 24. The second portion 35 extends from the first portion 33 to the third portion 37 and has a length that is less than the length 31 of the proximal portion 24. The third portion 37 extends from the second portion 35 to the proximal end 28 of the proximal portion 24 and has a length that is less than the length 31 of the proximal portion 24. The second portion 35 has a length that is greater than the length of the first portion 33 and the third portion 37.

The shaft 26 extends distally from the distal end 30 of the proximal portion 24 and has a proximal end 40, a tapered distal end 42, a first outside diameter 44 at the proximal end 40 of the shaft 26, and a second outside diameter 46 at the distal end 42 of the shaft 26. The shaft 26 has a length 41 that extends from the proximal end 40 to the distal end 42 of the shaft 26. The proximal end 40 of shaft 26 is attached to the distal end 30 of the proximal portion 24. The first outside diameter 44 is greater than the second outside diameter 46. The first outside diameter 44 is less than the first outside diameter 32 of the proximal portion 24. The body 22 of the elongate member 12 defines the first outside diameter 44 along a first portion 43 of the length 41 of the shaft 26 that extends from the proximal end 40 of the shaft 26 toward the distal end 42 of the shaft 26. The first portion 43 of the length 41 of the shaft 26 has a first outside 44 diameter that is constant. The first outside diameter 44 of the shaft 26 tapers to the second outside diameter 46 along a second portion 45 of the length 41 of the shaft 26 that extends from the first portion 43 to the distal end 42 of the shaft 26. The first portion 43 has a length that is less than the length 41 of the shaft 26 and greater than the length of the second portion 45.

In the illustrated embodiment, the length 21 of the elongate member 12 is equal to the sum of the length 31 of the proximal portion 24 and the length 41 of the shaft 26. The length 31 of the proximal portion 24 is less than the length 41 of the shaft 26.

Figure 4:
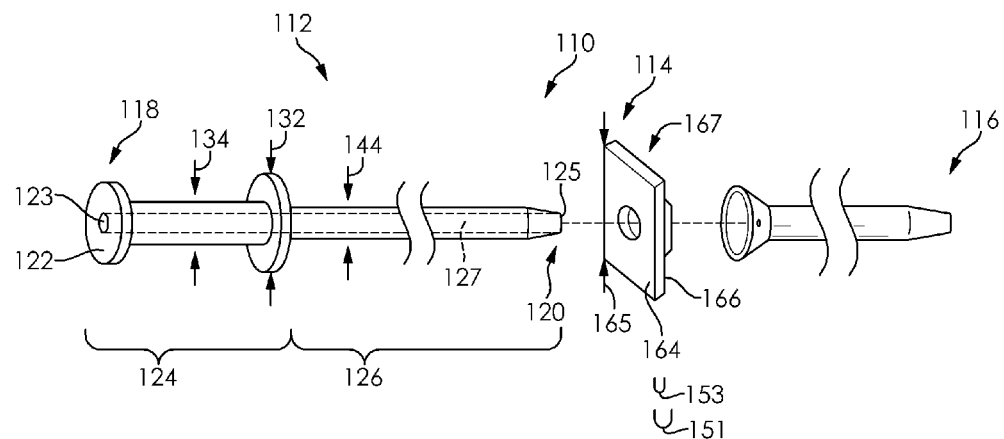
FIG. 4 illustrates another embodiment of a medical device.

While the elongate member 12 has been illustrated as having a particular structural arrangement, an elongate member can have any suitable structural arrangement. Skilled artisans will be able to select a suitable structural arrangement for an elongate member according to a particular embodiment based on various considerations, including the structural arrangement of an intermediate member and/or tubular member included in a medical device of which the elongate member is a component. Example structural arrangements considered suitable for the proximal portion of an elongate member include, but are not limited to, a proximal portion that has an outside diameter that is constant, or substantially constant, along a portion, or the entirety, of its length, a proximal portion that has an outside diameter along a portion, or the entirety, of its length that is equal to, or substantially equal to, the first outside diameter, or any outside diameter, of a shaft, a proximal portion that has an outside diameter that is equal to, or substantially equal to, the first outside diameter of a shaft and that defines one or more protuberances that extend outward and away from the body of the elongate member (e.g., each protuberance providing a mechanical stop to proximal advancement of an intermediate portion and/or tubular member along the elongate member), and any other structural arrangement considered suitable for a particular application. Example structural arrangements considered suitable for the shaft of an elongate member include, but are not limited to, a shaft that has a constant, or substantially constant, outside diameter along a portion, or the entirety, of its length, a shaft that omits the inclusion of a tapered distal end, a shaft that has a varying diameter along a portion, or the entirety, of its length, and any other structural arrangement considered suitable for a particular application. Optionally, an elongate member can define a lumen that extends through the proximal portion and the shaft, as shown in FIG. 4.

The shaft 26 can be attached to the distal end 30 of proximal portion 24 using any suitable method of attachment. Skilled artisans will be able to select a suitable method of attachment between the shaft and the proximal portion of an elongate member according to a particular embodiment based on various considerations, including the material(s) that forms the proximal portion and/or shaft. Examples of suitable methods of attachment considered suitable between the proximal portion and the shaft of an elongate member include, but are not limited to, using an adhesive, welding, fusing (e.g., heat fusing), threaded connections, integrated components, and any other method of attachment considered suitable for a particular application.

The elongate member 12 can be formed of any suitable material. Skilled artisans will be able to select a suitable material to form an elongate member according to a particular embodiment based on various considerations, including the material(s) that forms an intermediate member and/or a tubular member included in a medical device of which the elongate member is a component. Example materials considered suitable to form an elongate member include, but are not limited to, biocompatible materials, materials that can be made biocompatible, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polyethylene, polyurethane, silicone, and any other material considered suitable for a particular application.

In the illustrated embodiment, the intermediate member 14 is releasably disposed on shaft 26. The intermediate member 14 comprises a proximal end 52, a distal end 54, and a body 56. The intermediate member 14 has a length 51 that extends from the proximal end 52 to the distal end 54. The body 56 of the intermediate member 14 defines a first opening 58, a second opening 60, a lumen 62, a first surface 64, a second surface 66, a protuberance 68, and a support post 70. The first opening 58 is defined on the proximal end 52 and the second opening 60 is defined on the distal end 54. The lumen 62 extends from the first opening 58 to the second opening 60. Each of the first opening 58, second opening 60, and lumen 62 has an inside diameter that is sized and configured to receive the shaft 26. For example, each of the first opening 58, second opening 60, and lumen 62 has an inside diameter that is less than the first outside diameter 32 of proximal portion 24 and greater than the first outside diameter 44 of shaft 26.

The first surface 64 is opposably facing the second surface 66. The first surface 64 is disposed on the proximal end 52 of intermediate member 14 and the second surface 66 is disposed between the proximal end 52 and the distal end 54 of the intermediate member 14. A first portion 53 of the length 51 of the intermediate member 14 extends from the first surface 64 to the second surface 66. The first surface 64 and the second surface 66 cooperatively define a disc-shaped portion 67 of the intermediate member 14. The first surface 64 is circular and has an outside diameter 65 that is greater than the first outside diameter 32 of the proximal portion 24. The second surface 66 is circular and has an outside diameter that is equal to the outside diameter 65 of the first surface 64. While the first surface 64 has been illustrated as having an outside diameter that is equal to the outside diameter of the second surface 66, a first surface can have an outside diameter that is greater than, less than, or substantially equal to, the outside diameter of a second surface of an intermediate member.

The protuberance 68 extends distally from the second surface 66 and tapers from the second surface 66 to the distal end 54 of the intermediate member 14. In the illustrated embodiment, protuberance 68 is frustoconical. The second opening 60 is defined on protuberance 68. The protuberance 68 is complementary to a proximal portion 86' of the lumen 86 of the tubular member 16, as described in more detail herein. The support post 70 extends from protuberance 68 and away from the second surface 66 to a support post end 72 and has an outside diameter that is constant along the length of the support post 70. In the illustrated embodiment, support post 70 is cylindrical.

The intermediate member 14 can be formed of any suitable material. Skilled artisans will be able to select a suitable material to form an intermediate member according to a particular embodiment based on various considerations, including the material(s) that forms an elongate member and/or a tubular member included in a medical device of which the intermediate member is a component. Example materials considered suitable to form an intermediate member include, but are not limited to, biocompatible materials, materials that can be made biocompatible, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polyethylene, polyurethane, polyetheretherketone (PEEK), silicone, and any other material considered suitable for a particular application. Optionally, an intermediate member can be formed of a material that is flexible relative to a material that forms an elongate member and/or tubular member (e.g., intermediate member is formed of a material that is relatively more flexible than a material that forms an elongate member and/or tubular member).

While the intermediate member 14 has been illustrated as having a particular structural arrangement, an intermediate member can have any suitable structural arrangement. Skilled artisans will be able to select a suitable structural arrangement for an intermediate member according to a particular embodiment based on various considerations, including the structural arrangement of an elongate member and/or tubular member included in a medical device of which the intermediate member is a component. Example structural arrangements considered suitable for an intermediate member include, but are not limited to, intermediate members that omit the inclusion of a protuberance, intermediate members that omit the inclusion of a support post, intermediate members that omit the inclusion of a protuberance and a support post, and any other structural arrangement considered suitable for a particular application.

While the first surface 64 has been illustrated as opposably facing the second surface 66, the first surface of an intermediate member can be positioned such that it is substantially opposably facing the second surface of an intermediate member, or disposed at an angle to the second surface of an intermediate member. Skilled artisans will be able to select a suitable arrangement between the first surface and second surface of an intermediate member according to a particular embodiment based on various considerations, including the structural arrangement of an elongate member and/or tubular member in a medical device of which the intermediate member is a component.

While the first surface 64 and the second surface 66 have been illustrated as cooperatively defining a disc-shaped portion 67 of the intermediate member 14, the first surface and/or second surface of an intermediate member can have any suitable structural configuration. Skilled artisans will be able to select a suitable structural configuration for the first surface and/or second surface of an intermediate member according to a particular embodiment based on various considerations, including the structural arrangement of an elongate member and/or tubular member included in a medical device of which the intermediate member is a component. Example structural configurations considered suitable for a first surface and/or second surface of an intermediate member include, but are not limited to, a first surface and/or second surface that is circular, square, triangular, rectangular, oval, and any other structural configuration considered suitable for a particular application. The portion of an intermediate member that is cooperatively defined by the first surface and the second surface of an intermediate member can have any suitable geometric shape, such as a disc, cylinder, cuboid, cube, triangular prism, sphere, semi-sphere, and any other shape considered suitable for a particular application.

While each of the first opening 58, second opening 60, and lumen 62 has been illustrated as having an inside diameter that is greater than the first outside diameter 44 of shaft 26, the first opening, second opening, and/or lumen of an intermediate member can have any suitable diameter, such as a diameter that is greater than, equal to, substantially equal to, or less than the first outside diameter of a shaft. For example, when an intermediate member is formed of a material that is flexible relative to a material that forms an elongate member (e.g., the material that forms the intermediate member is relatively more flexible than the material that forms the elongate member), a first opening, second opening, and/or lumen can have a diameter that is equal to, substantially equal to, or less than the first outside diameter of a shaft. In these embodiments, the first opening, second opening, and/or lumen can expand when the shaft is passed through, or disposed within, the first opening, second opening, and/or lumen to provide a friction fit between the two components.

While the intermediate member 14 has been illustrated as having a frustoconical protuberance 68, the body of an intermediate member can define a protuberance having any suitable structural arrangement. Skilled artisans will be able to select a suitable structural arrangement for the protuberance of an intermediate member according to a particular embodiment based on various considerations, including the structural arrangement of a tubular member included in a medical device of which the intermediate member is a component. Example structural arrangements considered suitable for a protuberance of an intermediate member include, but are not limited to, a protuberance that extends along a portion, or the entirety, of the circumference of an opening defined by the body of the intermediate member, a protuberance that defines one or more edges, a protuberance that has a constant, or substantially constant, outside diameter along a portion, or the entirety, of its length, a protuberance that is a cylinder, cuboid, cube, triangular prism, sphere, semi-sphere, and any other structural arrangement considered suitable for a particular application.

While the intermediate member 14 has been illustrated as having a cylindrical support post 70, an intermediate member can have any suitable number of support posts and each support post can have any suitable structural arrangement. Skilled artisans will be able to select a suitable structural arrangement for a support post and a suitable number of support posts to include on an intermediate member according to a particular embodiment based on various considerations, including the structural arrangement of a tubular member included in a medical device of which the intermediate member is a component. Example structural arrangements considered suitable for a support post include, but are not limited to, a support post that has a constant, or substantially constant, outside diameter along a portion, or the entirety, of its length, a support post that has a varying diameter along its length, a support post that includes one or more protuberances along its length to assist with attachment to a tubular member, a support post that has a geometric shape, such as a cylinder, cuboid, cube, triangular prism, sphere, semi-sphere, and any other structural arrangement considered suitable for a particular application. Example number of support posts considered suitable to include on an intermediate member include, but are not limited to, one, at least one, two, a plurality, three, four, five, six, seven, and any other number considered suitable for a particular application. In embodiments in which one or more support posts are included, each support post can extend from the second surface of an intermediate member and/or from a protuberance defined by the body of the intermediate member.

In the illustrated embodiment, the tubular member 16 is releasably disposed on shaft 26 distal to the intermediate member 14. The tubular member 16 comprises a proximal end 76, a distal end 78, and a body 80. The tubular member has a length 75 that extends from the proximal end 76 to the distal end 78 and is less than the length 41 of the shaft 26. The body 80 of the tubular member 16 defines a first opening 82, a second opening 84, a lumen 86, a flared proximal portion 88, a tapered distal end 90, and a passageway 92. The first opening 82 is defined on the proximal end 76 and the second opening 84 is defined on the distal end 78. The lumen 86 extends from the first opening 82 to the second opening 84.

The first opening 82 has a first inside diameter 77 and second opening 84 has a second inside diameter 79. Thus, the lumen 86 has a first inside diameter 77 and a second inside diameter 79. The first inside diameter 77 is greater than the second inside diameter 79 and is greater than the first outside diameter 44 of shaft 26. The second inside diameter 79 is greater than the first outside diameter 44 of shaft 26. Alternatively, the second inside diameter of a tubular member can be equal to, substantially equal to, or less than the first outside diameter of a shaft such that a friction fit between the tubular member and shaft can be accomplished. The first inside diameter 77 tapers to the second inside diameter 79 along a first portion 81 of the length 75 of the tubular member 16 that extends from the proximal end 76 toward the distal end 78 to a location between the proximal end 76 and the distal end 78. The second inside diameter 79 extends along a second portion 83 of the length 75 of the tubular member 16 that extends from the first portion 81 to the distal end 78 of the tubular member 16. The proximal portion 86' of lumen 86 has a structural arrangement that is complementary to the structural arrangement of the protuberance 68 of the intermediate member 14 and is adapted to receive the protuberance 68. Alternatively, the proximal portion of the lumen of a tubular member can receive a portion of a protuberance defined by an intermediate member. The proximal portion 86' of lumen 86 is frustoconical and tapers from the proximal end 76 of the tubular member 16 toward the distal end 78.

The tubular member 16 has a first outside diameter 85, a second outside diameter 87, and a third outside diameter 89. The first outside diameter 85 is disposed on the proximal end 76, the second outside diameter 87 is disposed along a portion of the length 75 between the proximal end 76 and the distal end 78, and the third outside diameter 89 is disposed on the distal end 78. The first outside diameter 85 is greater than the second outside diameter 87 and is disposed proximal to the second outside diameter 87. The second outside diameter 87 is greater than the third outside diameter 89 and is disposed proximal to the third outside diameter 89. The first outside diameter 85 tapers to the second outside diameter 87 along a third portion 91 of the length 75 of the tubular member 16 that extends from the proximal end 76 toward the distal end 78 and defines the flared proximal portion 88. The flared proximal portion 88 acts as a mechanical stop to distal advancement of the tubular member 16 beyond tissue disposed outside of a bodily passage. The flared proximal portion 88 is frustoconical and tapers from the proximal end 76 of the tubular member 16 toward the distal end 78. The second outside diameter 87 extends along a fourth portion 93 of the length 75 of the tubular member 16 that extends from the first portion 91 toward the distal end 78. The second outside diameter 87 tapers to the third outside diameter 89 along a fifth portion 95 of the length 75 of the tubular member 16 and defines the tapered distal end 90.

The passageway 92 is disposed on the flared proximal portion 88 of tubular member 16 between the proximal end 76 and the distal end 78 of the tubular member 16. The passageway 92 extends through the flared proximal portion 88 and provides access to lumen 86. The passageway 92 has a diameter that is sized and configured to receive the support post 70 of the intermediate member 14. For example, the passageway 92 can have a diameter that is greater than the outside diameter of support post 70. The passageway 92 can have any suitable structural arrangement, such as a structural arrangement that is complementary to the structural arrangement of a support post defined by the body of an intermediate member. For example, a passageway can have a structural arrangement that defines any suitable geometric shape, such as a cylinder, cuboid, cube, triangular prism, sphere, semi-sphere, and any other structural arrangement considered suitable for a particular embodiment. In the illustrated embodiment, passageway 92 is cylindrical.

While the tubular member 16 has been illustrated as having a particular structural arrangement, a tubular member can have any suitable structural arrangement. Skilled artisans will be able to select a suitable structural arrangement for a tubular member according to a particular embodiment based on various considerations, including the structural arrangement of an elongate member and/or intermediate member included in a medical device of which the tubular member is a component. Example structural arrangements considered suitable for a tubular member include, but are not limited to, tubular members that omit the inclusion of a flared proximal portion, tubular members that omit the inclusion of a tapered distal end, tubular members that omit the inclusion of a flared proximal portion and a tapered distal end, tubular members that define a shoulder, or stepped, configuration alternative to a flared proximal portion, tubular members that have a constant, or substantially constant, outside diameter along a portion, or the entirety, of their length, tubular members that define a lumen that has a constant, or substantially constant, inside diameter along a portion, or the entirety, of its length, and any other structural arrangement considered suitable for a particular application. For example, a tubular member, such as those described herein, can include a completely circumferentially closed member, a member that defines a slit along the entirety, or a portion, of its length, a member that defines one or more, or a plurality, of perforations along its length, a sheath, and any other structural configuration considered suitable for a particular embodiment.

While the body 80 of tubular member 16 has been illustrated as defining a passageway 92 that extends through the flared proximal portion 88 of the tubular member 16, the body of a tubular member can define any suitable number of passageways and each passageway can extend through any suitable portion of a tubular member. Skilled artisans will be able to select a suitable number of passageways to define on a tubular member and a suitable location to position each passageway according to a particular embodiment based on various considerations, including the number of support posts defined by an intermediate member included in a medical device of which the tubular member is a component. Example number of passageways considered suitable to include on a tubular member include, but are not limited to, one, at least one, two, a plurality, three, four, five, six, seven, and any other number considered suitable for a particular application. Example locations considered suitable to define a passageway on a tubular member include, but are not limited to, on the flared proximal portion of a tubular member, between the proximal end and the distal end of a tubular member, on the tapered distal portion of a tubular member, and any other location considered suitable for a particular application. For example, one or more passageways can be defined on a proximal portion of a tubular member, on an intermediate portion of a tubular member, between the proximal and distal end of a tubular member, and/or on a distal portion of a tubular member.

A passageway defined by a tubular member can have any suitable diameter, such as a diameter that is greater than, equal to, substantially equal to, or less than the outside diameter of a support post defined by an intermediate member. For example, when a tubular member is formed of a material that is flexible relative to a material that forms an intermediate member (e.g., the material that forms the tubular member is relatively more flexible than the material that forms the intermediate member), a passageway can have a diameter that is equal to, substantially equal to, or less than the diameter of a support post. In these embodiments, the passageway can expand when the support post is passed through, or disposed within, the passageway to provide a friction fit between the two components.

The tubular member 16 can be formed of any suitable material. Skilled artisans will be able to select a suitable material to form a tubular member according to a particular embodiment based on various considerations, including the material(s) that forms an elongate member and/or an intermediate member included in a medical device of which the tubular member is a component. Example materials considered suitable to form a tubular member include, but are not limited to, biocompatible materials, materials that can be made biocompatible, biodegradable materials, bioabsorbable materials such as chitosan, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polyethylene, polyurethane, polytetrafluoroethylene (PTFE), silicone, and any other material considered suitable for a particular application.

Optionally, a tubular member can have a first portion that is rigid relative to a second portion when free of the elongate member and/or intermediate member included in a medical device of which the tubular member is a component. Thus, the second portion can be flexible relative to the first portion (e.g., the material that forms the second portion is relatively more flexible than the material that forms the first portion). The first portion can extend from the proximal end toward the distal end to a location disposed between the proximal end and the distal end. The second portion can extend from the location disposed between the proximal end and the distal end to the distal end of the tubular member. The first portion can be formed of a first material and the second portion can be formed of a second material. The first material can be the same as, or different than, the second material. For example, the first portion can be formed of a material that has a first durometer hardness and the second portion can be formed of a material that has a second durometer hardness. The second durometer hardness is less than the first durometer hardness. For example, a tubular member can have a distal end, or a distal portion that extends from the distal end toward the proximal end, that has a second durometer hardness that is less than a first durometer hardness at the proximal end, or along a proximal portion that extends from the proximal end toward the distal end. Optionally, a tubular member can have a flared proximal portion that has a first durometer hardness that is greater than a second durometer hardness of the portion of the tubular member that extends from the flared proximal portion to the distal end of the tubular member, or a location between the flared proximal portion and the distal end of the tubular member.

In embodiments in which the first portion is formed of a first material that is different than a second material that forms the second portion, the first portion and the second portion can be attached to one another using any suitable method of attachment. Examples of suitable methods of attachment considered suitable between a first portion and a second portion of a tubular member include, but are not limited to, using an adhesive, welding, fusing (e.g., heat fusing), threaded connections, and any other method of attachment considered suitable for a particular application.

When the medical device 10 is fully assembled, as illustrated in FIG. 1, the distal end 78 of the tubular member 16 is disposed proximal to the distal end 20 of the elongate member 12. In the illustrated embodiment, the second portion 45 of the length 41 of shaft 26 is disposed distal to the distal end 78 of the tubular member 16. In addition, the fifth portion 95 of the length 75 of tubular member 16 is disposed proximal to the second portion 45 of the length 41 of shaft 26. This structural arrangement provides an assembled medical device 10 that has a tapered distal end and provides a mechanism for reducing the trauma to a bodily passage as the medical device 10 is advanced into the bodily passage. Alternatively, a portion of the second portion of the length of a shaft can be disposed distal to the distal end of a tubular member and/or a portion of the fifth portion of the length of a tubular member can be disposed proximal to the a second portion of the length of a shaft.

When the medical device 10 is fully assembled, the intermediate member 14 is releasably disposed on shaft 26 between the distal end 30 of the proximal portion 24 and the proximal end 76 of tubular member 16. Thus, the intermediate member 14 is disposed between the proximal portion 24 and the tubular member 16. The tubular member 16 is releasably disposed on shaft 26 and is disposed distal to intermediate member 14 such that protuberance 68 is disposed within the proximal portion 86' of lumen 86 and the support post 70 of the intermediate member 14 is disposed through the passageway 92 defined by the body 80 of tubular member 16. The support post 70 has a length such that the support post end 72 is disposed distal to the passageway 92 defined by the tubular member 16. The lengthwise axis of the support post 70 is coaxial with the lengthwise axis of the passageway 92. Alternatively, a portion of a protuberance of an intermediate member can be disposed within the proximal portion of the lumen of a tubular member, a support post can be disposed within a passageway defined by the body of a tubular member, and/or the axis of a support post can be disposed such that it is not coaxial with the lengthwise axis of the passageway. When a support post defined by an intermediate member is disposed within, or through, a passageway defined by a tubular member, the tubular member is rotationally fixed relative to the intermediate member.

In the illustrated embodiment, the first outside diameter 65 of the first surface 64 is greater than the first outside diameter 32 of the proximal portion 24. This structural arrangement provides a pushing surface (e.g., the length of the first surface 64 that extends beyond the first outside diameter 32 of the proximal portion 24) that can be used to remove the intermediate member 14 and/or the tubular member 16 from the elongate member 12 during use. For example, after a portion of the medical device 10 (e.g., portion of shaft, portion of tubular member) has been introduced into a bodily passage, salivary duct, or a portion of the urinary tract, a distal force can be applied on the intermediate member 14 (e.g., first surface 64) to advance the intermediate member 14 and the tubular member 16 distally along the shaft 26 until each of the intermediate member 14 and tubular member 16 become free of the elongate member 12. Alternatively, after a portion of the medical device 10 (e.g., portion of shaft, portion of tubular member) has been introduced into a bodily passage, the position of the intermediate member 14 can be maintained relative to the tissue disposed outside of the bodily passage and/or the bodily passage while applying a proximal force on the elongate member 12 (e.g., proximal portion) to advance the elongate member 12 proximally until it becomes free of the intermediate member 14 and the tubular member 16. The tubular member 16 can be used to complete treatment on, or within, the bodily passage and can be left in the bodily passage for an interval of time, or removed subsequent to the treatment being performed. Optionally, the tubular member 16 can be sutured to the tissue disposed outside of the bodily passage and/or the bodily passage wall. This can be accomplished, for example, by using passageway 92, or any other passageway defined by the body of the tubular member.

Each of the elongate member 12, intermediate member 14, and tubular member 16 can be fabricated using any suitable method of manufacture. Skilled artisans will be able to select a suitable method of manufacture to fabricate an elongate member, intermediate member, and/or tubular member according to a particular embodiment based on various considerations, including the material(s) that forms each component. Example methods of manufacture considered suitable to fabricate an elongate member include, but are not limited to, extrusion processes, molding processes, and any other method considered suitable for a particular application.

Figure 3A:
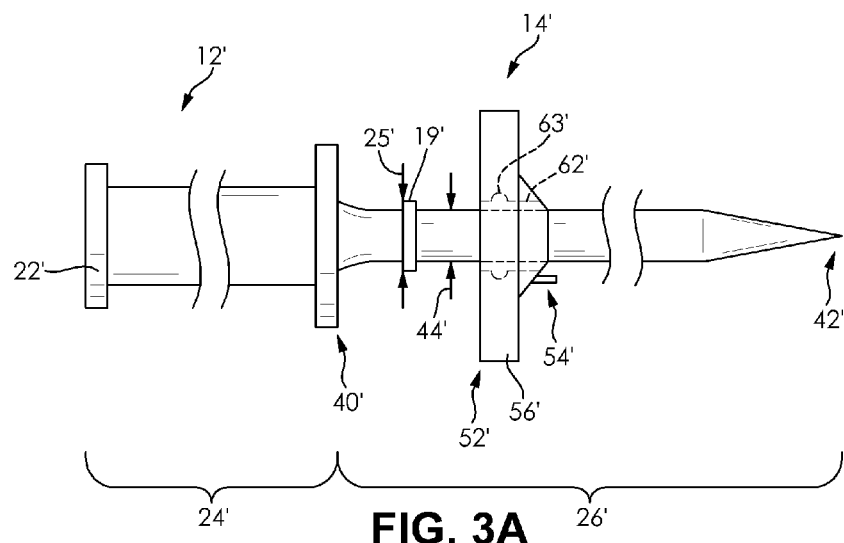
FIG. 3A illustrates a side view of another embodiment of an elongate member and intermediate member.

FIG. 3A illustrates another embodiment of an elongate member 12' and intermediate member 14'. The inclusion of a tubular member has been omitted from FIG. 3A for clarity. The elongate member 12' is similar to the elongate member 12 illustrated in FIGS. 1, 2, and 3 and described above, except as detailed below. The intermediate member 14' is similar to the intermediate member 14 illustrated in FIGS. 1, 2, and 3 and described above, except as detailed below. Reference numbers in FIG. 3A refer to the same structural element or feature referenced by the same number in FIGS. 1, 2, and 3, offset by '.

In this embodiment, the body 22' of the elongate member 12' defines a protuberance 19' between the proximal end 40' of the shaft 26' and the distal end 42' of the shaft 26'. The protuberance 19' extends outward and away from the shaft 26' and has an outside diameter 25' that is greater than the first outside diameter 44' of the shaft 26'. While the protuberance 19' is described as being defined by the body 22' of the elongate member 12', a protuberance can alternatively be a separate component attached to the shaft of an elongate member. For example, a protuberance can be a separate component attached to the shaft of an elongate member using any suitable method of attachment, such as welding, or by using adhesives.

While the elongate member 12' has been illustrated as having a protuberance 19', an elongate member can have any suitable number of protuberances, each having any suitable structural configuration. Skilled artisans will be able to select a suitable number of protuberances and a suitable structural arrangement for a protuberance according to a particular embodiment based on various considerations, including the structural arrangement of an intermediate member included in a medical device of which the elongate member is a component. Example number of protuberances considered suitable to include on an elongate member include, but are not limited to, one, at least one, two, a plurality, three, four, five, six, seven, and any other number considered suitable for a particular application. Example structural arrangements considered suitable for a protuberance include, but are not limited to, protuberances that extend about a portion, or the entirety, of the circumference of a shaft, protuberances that have an outside diameter that is greater than the first outside diameter of a shaft but less than the first outside diameter of the proximal portion of an elongate member, and any other structural arrangement considered suitable for a particular application.

In this embodiment, the body 56' of the intermediate member 14' defines a lumen 62' that has a recess 63' between the proximal end 52' and the distal end 54' of the intermediate member 14'. Recess 63' is sized and configured to receive protuberance 19'. For example, recess 63' has an inside diameter that is greater than the inside diameter of lumen 62'.

While the intermediate member 14' has been illustrated as having a recess 63', an intermediate member can have any suitable number of recesses, each having any suitable structural configuration. Skilled artisans will be able to select a suitable number of recesses and a suitable structural arrangement for a recess according to a particular embodiment based on various considerations, including the structural arrangement of an elongate member included in a medical device of which the intermediate member is a component. Example number of recesses considered suitable to include on an intermediate member include, but are not limited to, one, at least one, two, a plurality, three, four, five, six, seven, and any other number considered suitable for a particular application. Example structural arrangements considered suitable for a recess include, but are not limited to, recesses that extend about a portion, or the entirety, of the circumference of the lumen of an intermediate member, recesses that have an inside diameter that is greater than the inside diameter of the lumen of an intermediate member but less than the outside diameter of the first surface of an intermediate member, and any other structural arrangement considered suitable for a particular application.

In use, the protuberance 19' and recess 63' provide a mechanism for releasably attaching intermediate member 14' to elongate member 12'. For example, the shaft 26' of elongate member 12' can be passed through lumen 62' such that protuberance 19' is disposed within recess 63'. The intermediate member 14' can be formed of a material that is flexible relative to a material that forms elongate member 12' (e.g., the material that forms the intermediate member is relatively more flexible than the material that forms the elongate member) such that lumen 62' can expand when protuberance 19' is passed through the portion of lumen 62' disposed proximal to recess 63'.

FIG. 4 illustrates another medical device 110. Medical device 110 is similar to the medical device 10 illustrated in FIGS. 1, 2, and 3 and described above, except as detailed below. Reference numbers in FIG. 4 refer to the same structural element or feature referenced by the same number in FIGS. 1, 2, and 3, offset by 100. Thus, the medical device 110 comprises an elongate member 112, an intermediate member 114, and a tubular member 116.

In this embodiment, the body 122 of the elongate member 112 defines a first opening 123, a second opening 125, and a lumen 127. The first opening 123 is disposed on the proximal end 118 of the elongate member 112. The second opening 125 is disposed on the distal end 120 of the elongate member 112. The lumen 127 extends from the first opening 123 to the second opening 125 and through the proximal portion 124 and the shaft 126. Each of the first opening 123, second opening 125, and lumen 127 has an inside diameter that is less than the second outside diameter 134 of proximal portion 124 and the first outside diameter 144 of shaft 126. Any suitable device can be passed through lumen 127, such as a guide wire. Alternatively, any suitable device can be disposed within the lumen defined by an elongate member.

In this embodiment, the first surface 164 and the second surface 166 of the intermediate member 114 cooperatively define a cuboid portion 167 of the intermediate member 114 in which each of the first surface 164 and second surface 166 are square. A first portion 153 of the length 151 of the intermediate member 114 extends from the first surface 164 to the second surface 166. The first surface 164 has an outside diameter 165 that is greater than the first outside diameter 132 of the proximal portion 124 and the second surface 166 has an outside diameter that is equal to the outside diameter 165 of the first surface 164.

Figure 5:
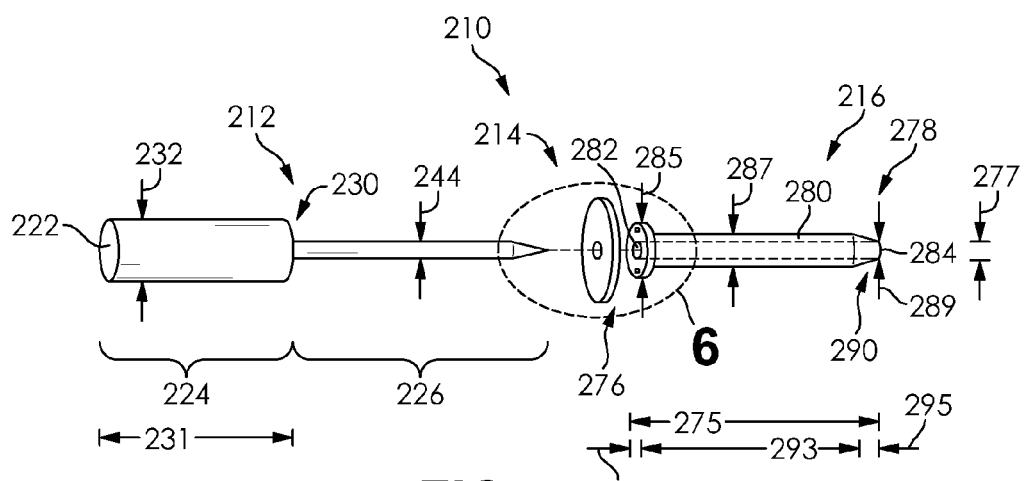
FIG. 5 illustrates another embodiment of a medical device.
Figure 6:
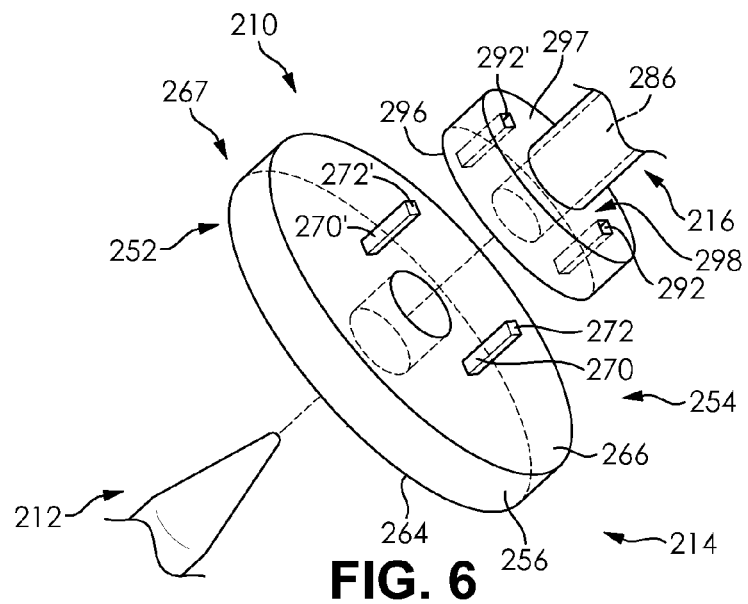
FIG. 6 is a magnified view of area 6 illustrated in FIG. 5.

FIGS. 5 and 6 illustrate another medical device 210. Medical device 210 is similar to the medical device 10 illustrated in FIGS. 1, 2, and 3 and described above, except as detailed below. Reference numbers in FIGS. 5 and 6 refer to the same structural element or feature referenced by the same number in FIGS. 1, 2, and 3, offset by 200. Thus, the medical device 210 comprises an elongate member 212, an intermediate member 214, and a tubular member 216.

In the illustrated embodiment, the elongate member 212 has a body 222 that defines a proximal portion 224 and a shaft 226 that extends distally from the distal end 230 of the proximal portion 224. The proximal portion 224 has an outside diameter 232 that is constant along the length 231 of the proximal portion 224. The outside diameter 232 of the proximal portion 224 is greater than the first outside diameter 244 of the shaft 226.

In the illustrated embodiment, the intermediate member 214 omits the inclusion of a protuberance (e.g., protuberance 68) and the body 256 of the intermediate member 214 defines a first support post 270 and a second support post 270'. The first surface 264 is disposed on the proximal end 252 of the intermediate member 214 and the second surface 266 is disposed on the distal end 254 of the intermediate member 214. The first support post 270 extends from the second surface 266 and away from the first surface 264 to a first support post end 272 and the second support post 270' extends from the second surface 266 and away from the first surface 264 to a second support post end 272'. Each of the first support post 270 and second support post 270' is cuboidal. In the illustrated embodiment, the first support post 270 has a length that is equal to the length of the second support post 270'. The first support post 270 has a first lengthwise axis that extends through its length that is parallel to a second lengthwise axis that extends through the length of the second support post 272'. However, other structural arrangements are considered suitable, such as structural arrangements in which the first lengthwise axis is substantially parallel, or not parallel, to the second lengthwise axis.

While first support post 270 has been illustrated as having a length that is equal to the length of the second support post 270', a support post can have any suitable length. Skilled artisans will be able to select a suitable length for a support post according to a particular embodiment based on various considerations, including the structural arrangement of a tubular member included in a medical device of which the intermediate member is a component. Example lengths considered suitable for a support post include, but are not limited to, a first support post that has a length that is greater than, equal to, substantially equal to, or less than the length of a second support post.

In the illustrated embodiment, the tubular member 216 omits the inclusion of a flared proximal portion (e.g., flared proximal portion 88) and has a body 280 that defines a first opening 282, a second opening 284, a lumen 286, a tapered distal portion 290, a first passageway 292, a second passageway 292', a first surface 296, and a second surface 297. The first opening 282 is defined on the proximal end 276 and the second opening 284 is defined on the distal end 278. The lumen 286 extends from the first opening 282 to the second opening 284. Each of the first opening 282, second opening 284, and lumen 286 has an inside diameter 277 that is greater than the first outside diameter 244 of shaft 226.

The first surface 296 is opposably facing the second surface 297. Alternatively, the first surface of a tubular member can be substantially opposably facing the second surface, or disposed at an angle to the second surface. The tubular member 216 has a first outside diameter 285, a second outside diameter 287, and a third outside diameter 289. The first outside diameter 285 is greater than the second outside diameter 287 and the second outside diameter 287 is greater than the third outside diameter 289. The first outside diameter 285 extends from the first surface 296 to the second surface 297. The first outside diameter 285 extends along a first portion 291 of the length 275 of the tubular member 216 that extends from the proximal end 276 to the second surface 297. The second outside diameter 287 extends along a second portion 293 of the length 275 of the tubular member 216 that extends from the first portion 291 (e.g., the second surface 297) toward the distal end 278. The second outside diameter 287 tapers to the third outside diameter 289 along a third portion 295 of the length 275 of the tubular member 216 that extends from the second portion 293 to the distal end 278 of the tubular member 216. This structural arrangement of the tubular member 216 defines a shoulder 298 between the proximal end 276 and the distal end 278 of the tubular member 216. During use, the shoulder 298 acts as a mechanical stop to distal advancement of the tubular member 216 beyond the tissue disposed outside of the bodily passage.

The first passageway 292 extends from an opening defined on the first surface 296 to an opening defined on the second surface 297. The second passageway 292' extends from an opening defined on the first surface 296 to an opening defined on the second surface 297. The first passageway 292 has an inside diameter that is greater than the outside diameter of the first support post 270 and the second passageway 292' has an inside diameter that is greater than the outside diameter of the second support post 270'. Alternatively, the first passageway and/or second passageway defined by a tubular member can have an inside diameter that is equal to, substantially equal to, or less than the outside diameter of a support post such that a friction fit between the intermediate member and tubular member can be accomplished. The first passageway 292 has a structural arrangement that is complementary to the first support post 270 and the second passageway 292' has a structural arrangement that is complementary to the second support post 270'. In the illustrated embodiment, each of the first passageway 292 and second passageway 292' is cuboidal. The first passageway 292 has a first lengthwise axis and the second passageway 292' has a second lengthwise axis. The first lengthwise axis is parallel to the second lengthwise axis. However, other structural arrangements are considered suitable, such as structural arrangements in which the first lengthwise axis is substantially parallel, or not parallel, to the second lengthwise axis.

When the medical device 210 is fully assembled, the intermediate member 214 is releasably disposed on the shaft 226 between the distal end 230 of the proximal portion 224 and the proximal end 276 of tubular member 216. Thus, the intermediate member 214 is disposed between the proximal portion 224 and the tubular member 216. The tubular member 216 is releasably disposed on shaft 226 and is disposed distal to the intermediate member 214 such that the first support post 270 is disposed through the first passageway 292 and the second support post 270' is disposed through the second passageway 292'. The lengthwise axis of the first support post 270 is coaxial with the lengthwise axis of the first passageway 292 and the lengthwise axis of the second support post 270' is coaxial with the lengthwise axis of the second passageway 292'. Alternatively, the lengthwise axis of the support post of an intermediate member can be disposed at an angle to the lengthwise axis of a passageway defined by a tubular member. When the first support post 270 is disposed through the first passageway 292 and the second support post 270' is disposed through the second passageway 292', the tubular member 216 is rotationally fixed relative to the intermediate member 214.

Various methods of treatment are described herein. While the methods described herein are shown and described as a series of acts, it is to be understood and appreciated that the methods are not limited by the order of acts, as some acts may in accordance with these methods, occur in different orders, and/or concurrently with other acts described herein.

Figure 7:
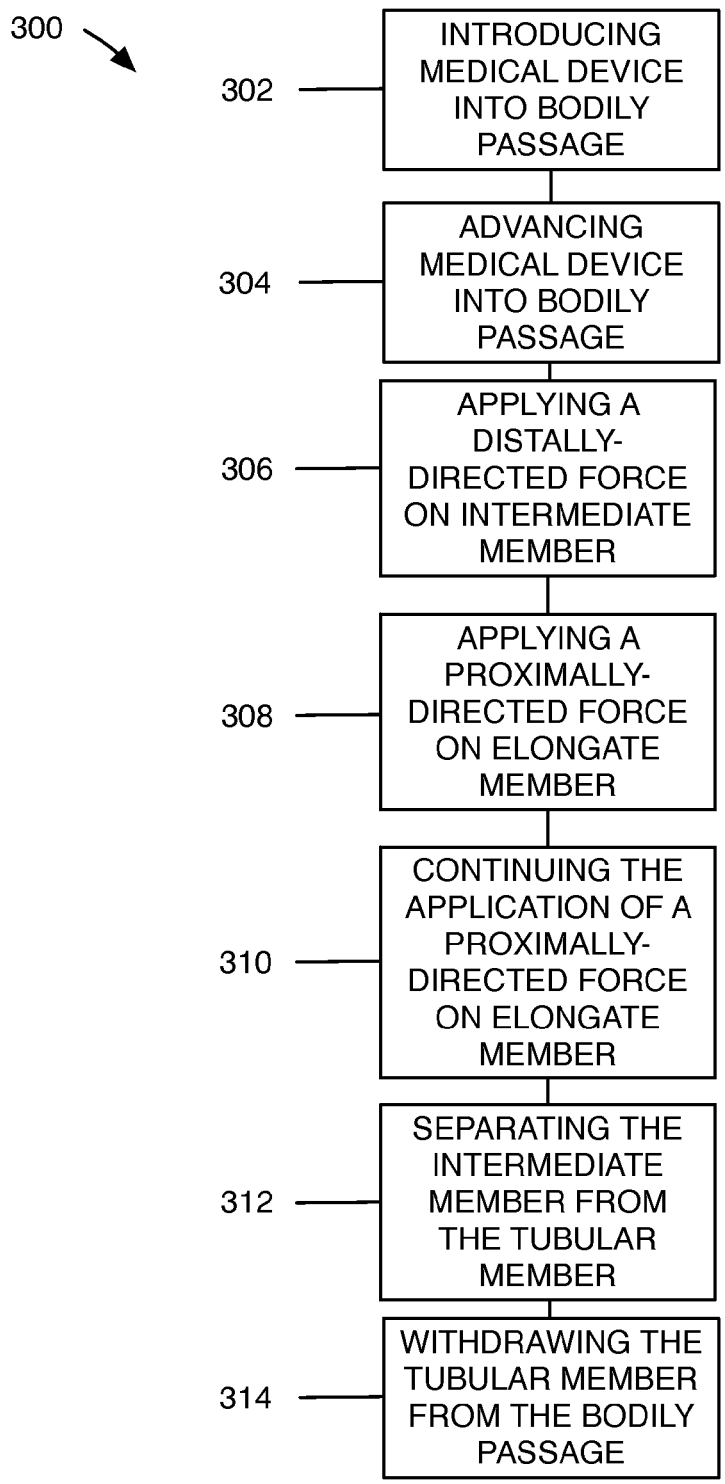
FIG. 7 is a flowchart representation of a method of treatment.

FIG. 7 is a flowchart representation of a method 300 of treating a bodily passage.

A step 302 comprises introducing a medical device having a medical device proximal end and a medical device distal end into a bodily passage such that the medical device distal end is disposed within the bodily passage. The bodily passage is defined by a bodily passage wall. Another step 304 comprises advancing the medical device into the bodily passage until the second outside diameter of the tubular member is disposed within the bodily passage. Another step 306 comprises applying a distally-directed force on the intermediate member. Another step 308 comprises applying a proximally-directed force on the elongate member while applying a distally-directed force on the intermediate member such that the elongate member is advanced proximally relative to the intermediate member and the tubular member. Another step 310 comprises continuing the application of a proximally-directed force on the elongate member while applying a distally-directed force on the intermediate member until the elongate member is free of the intermediate member and the tubular member. Another step 312 comprises separating the intermediate member from the tubular member. Another step 314 comprises withdrawing the tubular member from the bodily passage.

Step 302 can be accomplished using any suitable medical device according to an embodiment, such as the embodiments described and illustrated herein. Skilled artisans will be able to select a suitable medical device to introduce into a bodily passage according to a particular embodiment based on various considerations, including the treatment intended to be performed. Examples of medical devices considered suitable to introduce into a bodily passage to complete one or more steps and/or methods described herein include, but are not limited to, medical device 10, medical device 110, medical device 210, variations of medical device 10, medical device 110, and medical device 210, and any other medical device considered suitable for a particular application.

Step 302 can be accomplished by introducing a medical device into any suitable bodily passage. Skilled artisans will be able to select a suitable bodily passage to introduce a medical device according to a particular embodiment based on various considerations, including the treatment intended to be performed. Example bodily passages considered suitable to introduce a medical device include, but are not limited to, a salivary duct, a portion of the urinary tract, and any other bodily passage considered suitable for a particular application.

Step 304 can be accomplished by applying a distally-directed force (e.g., toward the bodily passage) on any suitable portion of the medical device such that the medical device is advanced into the bodily passage and the second outside diameter of the tubular member is disposed within the bodily passage. For example, a distally-directed force can be applied to an elongate member of an embodiment, such as elongate member 12, elongate member 12', elongate member 112, or elongate member 212.

An optional step comprises advancing the medical device into the bodily passage such that the flared proximal portion of the tubular member contacts tissue disposed outside of the bodily passage. This step can be accomplished by placing a distally-directed force on any suitable portion of the medical device until the distal surface of the flared proximal portion contacts the tissue disposed outside of the bodily passage. Alternatively, if the tubular member omits the inclusion of a flared proximal portion, such as tubular member 216, an optional step comprises advancing the medical device into the bodily passage such that the second surface of the tubular member contacts tissue disposed outside of the bodily passage. This step can be accomplished by placing a distally-directed force on any suitable portion of the medical device until the distal surface of second surface of the tubular member contacts the tissue disposed outside of the bodily passage.

Step 306 can be accomplished by applying a distally-directed force on the intermediate member such that the intermediate member is advanced toward and/or contacts tissue disposed outside of the bodily passage. The distally-directed force can be applied to any suitable portion of an intermediate member, such as the outside perimeter of the intermediate member, and/or the first surface of an intermediate member (e.g., first surface 64, first surface 164, first surface 264).

Alternative to applying a distally-directed force on the intermediate member, an alternative step comprises maintaining the position of the intermediate member relative to the tubular member. This step can be accomplished by applying any suitable force on the intermediate member such that the position of the intermediate member is maintained relative to the tubular member, the tissue disposed outside of the bodily passage, and/or the bodily passage.

Step 308 can be accomplished by applying a proximally-directed force on any suitable portion of the elongate member while applying a distally-directed force on the intermediate member such that the elongate member is advanced proximally relative to the intermediate member and tubular member and is advanced proximally through the lumen defined by the tubular member. For example, step 308 can be accomplished concurrently with step 306. Proximally-directed force can be applied to proximal portion 24, proximal portion 24', proximal portion 124, proximal portion 224, or any other portion of an elongate member considered suitable for a particular application.

Alternative to applying a proximally-directed force on the elongate member while applying a distally-directed force on the intermediate member, an alternative step comprises applying a proximally-directed force on the elongate member while maintaining the position of the intermediate member relative to the tubular member such that the elongate member is advanced proximally relative to the intermediate member and the tubular member and advanced proximally through the lumen defined by the tubular member.

Step 310 can be accomplished by continuing the application of a proximally-directed force on the elongate member while applying a distally-directed force on the intermediate member until the distal end of the shaft is disposed proximal to the proximal end of the intermediate member and the elongate member is free of the tubular member and the intermediate member.

Alternative to continuing the application of a proximally-directed force on the elongate member while applying a distally-directed force on the intermediate member, an alternative step comprises continuing the application of a proximally-directed force on the elongate member while maintaining the position of the intermediate member relative to the tubular member until the distal end of the shaft is disposed proximal to the proximal end of the intermediate member and the elongate member is free of the intermediate member and the tubular member.

Step 312 can be accomplished by applying a proximally-directed force on any suitable portion of the intermediate member (e.g., disc-shaped portion 67, cuboid portion 167) such that the support post is withdrawn from the passageway defined by the tubular member. Alternatively, if the intermediate member includes more than one support post and the tubular member defines more than one passageway (e.g., intermediate member 214, tubular member 216), this step can be accomplished by applying a proximally-directed force on any suitable portion of the intermediate member such that each of the support posts is withdrawn from its respective passageway.

Step 314 can be accomplished by applying a proximally-directed force on the tubular member until it has been withdrawn from the bodily passage such that the distal end of the tubular member is disposed proximal to the bodily passage. Optionally, step 314 can be omitted from method 700. For example, step 314 can be omitted in embodiments in which the tubular member is formed of a biodegradable or bioabsorbable material.

An optional step that can be completed prior to withdrawing the tubular member from the bodily passage comprises suturing the tubular member to tissue that is disposed outside of the bodily passage. This step can be accomplished by passing a suture through the passageway defined by the tubular member and through the tissue that is disposed outside of the bodily passage to secure the tubular member to the tissue and within the bodily passage. In embodiments in which the body of the tubular member defines more than one passageway, an optional step than can be completed prior to withdrawing the tubular member from the bodily passage comprises passing a suture through each passageway, or one or more of the passageways, and through the tissue that is disposed outside of the bodily passage to secure the tubular member to the wall that defines the bodily passage.

Alternatively, an optional step that can be completed prior to withdrawing the tubular member from the bodily passage comprises suturing the tubular member to the wall that defines the bodily passage. This step can be accomplished by passing a suture through the passageway defined by the tubular member and through the bodily passage wall to secure the tubular member to the bodily passage wall and within the bodily passage. In embodiments in which the body of the tubular member defines more than one passageway, an optional step than can be completed prior to withdrawing the tubular member from the bodily passage comprises passing a suture through each passageway, or one or more of the passageways, and through the bodily passage wall to secure the tubular member to the bodily passage wall.

An optional step that can be completed prior to withdrawing the tubular member from the bodily passage comprises leaving the tubular member in the bodily passage for an interval of time. Any suitable interval of time is considered suitable, and skilled artisans will be able to select a suitable interval of time to leave a tubular member in a bodily passage according to a particular embodiment based on various considerations, including the treatment intended to be performed. Example intervals of time considered suitable to leave a tubular member within a bodily passage include, but are not limited to, one or more minutes, one or more hours, one or more days, and any other interval of time considered suitable for a particular application.

Another optional step that can be completed prior to withdrawing the tubular member from the bodily passage comprises passing a medication and/or medical device through the lumen defined by the tubular member and into the bodily passage to perform treatment. Alternatively, a medical device can be passed through a portion of the lumen defined by the tubular member. This step can be accomplished using any suitable medication and/or medical device, and skilled artisans will be able to select a suitable medication and/or medical device to pass through the entirety, or a portion, of a tubular member according to a particular embodiment based on various considerations, including the treatment intended to be performed. Example medical devices considered suitable to pass through the lumen defined by a tubular member include, but are not limited to, suction catheters, balloon catheters, irrigation catheters, a camera, a light source, and any other medical device considered suitable for a particular application. Another optional step comprises performing treatment with a medical device that has been passed through a portion, or the entirety, of the lumen defined by the tubular member. Another optional step comprises withdrawing the medical device from the lumen defined by the tubular member.

While various steps, alternative steps, and optional steps have been described above with respect to treating a bodily passage, these steps, alternative steps, and optional steps can be included in, accomplished concurrently with, and/or accomplished in the alternative to, the methods, steps, alternative steps, and/or optional steps described below with respect to treating a bodily passage.

Figure 8:
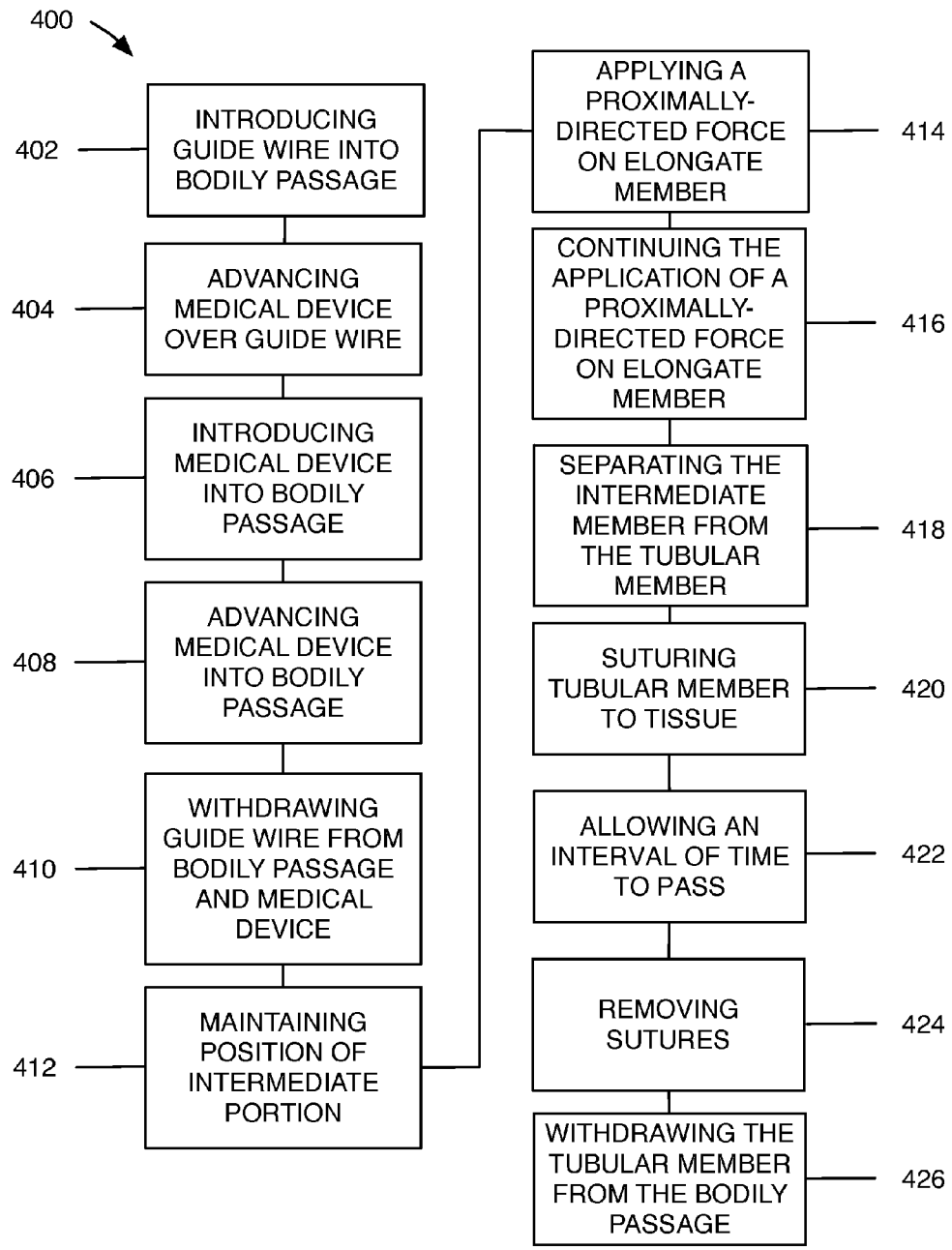
FIG. 8 is a flowchart representation of another method of treatment.

FIG. 8 is a flowchart representation of a method 400 of treating a bodily passage.

A step 402 comprises introducing a guide wire having a guide wire proximal end and a guide wire distal end into a bodily passage such that the guide wire distal end is disposed within the bodily passage. The bodily passage is defined by a bodily passage wall. Another step 404 comprises advancing a medical device having a medical device proximal end and a medical device distal end over the guide wire such that the guide wire is disposed within a lumen defined by an elongate member of the medical device. Another step 406 comprises introducing the medical device into the bodily passage such that the medical device distal end is disposed within the bodily passage. Another step 408 comprises advancing the medical device into the bodily passage until the second outside diameter of the tubular member is disposed within the bodily passage. Another step 410 comprises withdrawing the guide wire from the bodily passage and the medical device. Another step 412 comprises maintaining the position of the intermediate member relative to the tubular member. Another step 414 comprises applying a proximally-directed force on the elongate member while maintaining the position of the intermediate member such that the elongate member is advanced proximally relative to the intermediate member and the tubular member. Another step 416 comprises continuing the application of a proximally-directed force on the elongate member while maintaining the position of the intermediate member until the elongate member is free of the intermediate member and the tubular member. Another step 418 comprises separating the intermediate member from the tubular member. Another step 420 comprises suturing the tubular member to tissue. Another step 422 comprises allowing an interval of time to pass. Another step 424 comprises removing the sutures from the tissue and the tubular member. Another step 426 comprises withdrawing the tubular member from the bodily passage.

Step 402 can be accomplished using any suitable guide wire having any suitable length and structural arrangement. Skilled artisans will be able to select a guide wire to introduce into a bodily passage according to a particular embodiment based on various considerations, including the treatment intended to be performed. Step 402 can be accomplished by applying a distally-directed force (e.g., toward the bodily passage) on any suitable portion of the guide wire such that the guide wire distal end is advanced into the bodily passage.

Step 402 can be accomplished by introducing a guide wire into any suitable bodily passage. Skilled artisans will be able to select a suitable bodily passage to introduce a guide wire according to a particular embodiment based on various considerations, including the treatment intended to be performed. Example bodily passages considered suitable to introduce a guide wire include, but are not limited to, a salivary duct, a portion of the urinary tract, and any other bodily passage considered suitable for a particular application.

Step 404 can be accomplished using any suitable medical device according to an embodiment, such as the embodiments described and illustrated herein. Skilled artisans will be able to select a suitable medical device to advance over a guide wire according to a particular embodiment based on various considerations, including the treatment intended to be performed. Examples of medical devices considered suitable to advance over a guide wire to complete one or more steps and/or methods described herein include, but are not limited to, medical devices, such as medical device 110, medical devices that include an elongate member that defines a lumen that extends from the proximal end of the elongate member to the distal end of the elongate member (e.g., elongate member 112), and any other medical device considered suitable for a particular application. Any of the medical devices described and illustrated herein are considered suitable and can include an elongate member that defines a lumen that extends from an opening defined on the proximal end of the elongate member to an opening defined on the distal end of the elongate member.

Step 404 can be accomplished by passing the proximal end of the guide wire through a distal opening of the lumen defined by the elongate member (e.g., lumen 127 of elongate member 112) and applying a distally-directed force on any suitable portion of the medical device such that the guide wire is passed through the a proximal opening of the lumen and the medical device is disposed on the guide wire.

Step 406 can be accomplished by applying a distally-directed force on any suitable portion of the medical device such that the medical device distal end is advanced distally over the guide wire and introduced into the bodily passage.

Step 408 can be accomplished by applying a distally-directed force on any suitable portion of the medical device such that the medical device distal end is advanced into the bodily passage, over the guide wire, and the second outside diameter of the tubular member is disposed within the bodily passage. For example, a distally-directed force can be applied to an elongate member of an embodiment, such as elongate member 12, elongate member 12', elongate member 112, or elongate member 212.

An optional step comprises advancing the medical device into the bodily passage such that the flared proximal portion of the tubular member contacts tissue disposed outside of the bodily passage. This step can be accomplished by placing a distally-directed force on any suitable portion of the medical device until the distal surface of the flared proximal portion contacts the tissue disposed outside of the bodily passage. Alternatively, if the tubular member omits the inclusion of a flared proximal portion, such as tubular member 216, an optional step comprises advancing the medical device into the bodily passage such that the second surface of the tubular member contacts tissue disposed outside of the bodily passage. This step can be accomplished by placing a distally-directed force on any suitable portion of the medical device until the second surface of the tubular member contacts the tissue disposed outside of the bodily passage.

Step 410 can be accomplished by applying a proximally-directed force on any suitable portion of the guide wire such that the guide wire is withdrawn from the bodily passage and the lumen defined by the elongate member.

Step 412 can be accomplished by maintaining the position of the intermediate member relative to the tubular member. This step can be accomplished by applying any suitable force (e.g., distally-directed, proximally-directed, radially-directed) on the intermediate member such that the position of the intermediate member is maintained relative to the tubular member, the tissue disposed outside of the bodily passage, and/or the bodily passage.

Step 414 can be accomplished by applying a proximally-directed force (e.g., away from the bodily passage) on any suitable portion of the elongate member while maintaining the position of the intermediate member relative to the tubular member such that the elongate member is advanced proximally relative to the intermediate member and tubular member and is advanced proximally through the lumen defined by the tubular member. For example, the step 414 can be accomplished concurrently with step 412. Proximally-directed force can be applied to proximal portion 24, proximal portion 24', proximal portion 124, proximal portion 224, or any other portion of an elongate member considered suitable for a particular application.

Step 416 can be accomplished by continuing the application of a proximally-directed force on the elongate member while maintaining the position of the intermediate member relative to the tubular member until the distal end of the shaft is disposed proximal to the proximal end of the intermediate member and the elongate member is free of the intermediate member and the tubular member.

Step 418 can be accomplished by applying a proximally-directed force on any suitable portion of the intermediate member (e.g., disc-shaped portion 67, cuboid portion 167) such that the support post is withdrawn from the passageway defined by the tubular member. Alternatively, if the intermediate member includes more than one support post and the tubular member defines more than one passageway (e.g., intermediate member 214, tubular member 216), this step can be accomplished by applying a proximally-directed force on any suitable portion of the intermediate member such that each of the support posts is withdrawn from its respective passageway.

Step 420 can be accomplished by suturing the tubular member to tissue that is disposed outside of the bodily passage. This step can be accomplished by passing one or more sutures through the passageway defined by the tubular member and through the tissue that is disposed outside of the bodily passage to secure the tubular member to the tissue and within the bodily passage. In embodiments in which the body of the tubular member defines more than one passageway, an alternative step than can be completed prior to withdrawing the tubular member from the bodily passage comprises passing one or more sutures through each passageway, or one or more of the passageways, and through the tissue that is disposed outside of the bodily passage to secure the tubular member to the wall that defines the bodily passage.

A step that can be completed in addition, or alternative to, step 420 comprises suturing the tubular member to tissue that defines the bodily passage. This step can be accomplished by passing one or more sutures through a passageway defined by the tubular member and through the tissue that defines the bodily passage to secure the tubular member to the tissue and within the bodily passage. In embodiments in which the body of the tubular member defines more than one passageway, an alternative step that can be completed prior to withdrawing the tubular member from the bodily passage comprises passing one or more sutures through each passageway, or one or more of the passageways, and through the tissue that defines the bodily passage to secure the tubular member to the wall that defines the bodily passage.

Step 422 can be accomplished by allowing an interval of time to pass before removing the sutures and withdrawing the tubular member from the bodily passage. Any suitable interval of time is considered suitable, and skilled artisans will be able to select a suitable interval of time to leave a tubular member in a bodily passage according to a particular embodiment based on various considerations, including the treatment intended to be performed. Example intervals of time considered suitable to leave a tubular member within a bodily passage include, but are not limited to, one or more minutes, one or more hours, one or more days, and any other interval of time considered suitable for a particular application.

Step 424 can be accomplished by removing the one or more sutures such that the tubular member can be removed from the bodily passage. Optionally, step 424 can be omitted from method 800. For example, step 424 can be omitted in embodiment in which the one or more sutures are formed of a biodegradable or bioabsorbable material.

Step 426 can be accomplished by applying a proximally-directed force on the tubular member until it has been withdrawn from the bodily passage such that the distal end of the tubular member is disposed proximal to the bodily passage. Optionally, step 426 can be omitted from method 800. For example, step 426 can be omitted in embodiments in which the tubular member is formed of a biodegradable or bioabsorbable material.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A medical device for the treatment of a bodily passage, said medical device comprising:
    an elongate member having a proximal portion and a shaft extending distally from the proximal portion, the proximal portion having a first outside diameter, the shaft having a first proximal end attached to the proximal portion, and a first distal end, the shaft having a second outside diameter that is less than the first outside diameter;
    an intermediate member releasably disposed on the shaft and having a second proximal end, a second distal end, an intermediate member body, and a third outside diameter that is greater than the first outside diameter of the proximal portion, the intermediate member body defining a first intermediate member opening on the second proximal end, a second intermediate member opening on the second distal end, and an intermediate member lumen extending from the first intermediate member opening to the second intermediate member opening, the intermediate member lumen having an inside diameter that is less than the first outside diameter of the proximal portion; and
    a tubular member releasably disposed on the shaft distal to the intermediate member, the tubular member separable from the intermediate member and having a third proximal end, a third distal end, and a tubular member body defining a first tubular member opening on the third proximal end, a second tubular member opening on the third distal end, and a tubular member lumen extending from the first tubular member opening to the second tubular member opening,
    wherein the tubular member body defines a passageway that extends through the tubular member body and provides access to the tubular member lumen,
    wherein the tubular member has a frustoconical proximal portion that tapers from the third proximal end toward the third distal end;
    wherein the tubular member lumen has a frustoconical proximal portion that tapers from the third proximal end toward the third distal end;
    wherein the intermediate member body defines a first surface, a second surface, a frustoconical protuberance, and a support post, the first surface disposed on the second proximal end and opposably facing the second surface, the frustoconical protuberance extending distally from the second surface and tapering from the second surface toward the second distal end, the support post extending distally from the frustoconical protuberance to a support post end;
    wherein the frustoconical protuberance is disposed within the frustoconical proximal portion of the tubular member lumen; and
    wherein the support post is disposed within the passageway defined by the tubular member body.

2. A medical device for the treatment of a bodily passage, said medical device comprising:
- an elongate member having a proximal portion and a shaft extending distally from the proximal portion, the proximal portion having a first outside diameter, the shaft having a first proximal end attached to the proximal portion, a tapered first distal end, and a length extending from the first proximal end to the first distal end, the shaft having a second outside diameter that is less than the first outside diameter;
- an intermediate member releasably disposed on the shaft and having a second proximal end, a second distal end, an intermediate member body, and a third outside diameter that is greater than the first outside diameter of the proximal portion, the intermediate member body defining a first intermediate member opening on the second proximal end, a second intermediate member opening on the second distal end, and an intermediate member lumen extending from the first intermediate member opening to the second intermediate member opening, the intermediate member lumen having an inside diameter that is less than the first outside diameter of the proximal portion; and
- a tubular member releasably disposed on the shaft distal to the intermediate member, the tubular member separable from the intermediate member and having a third proximal end, a tapered third distal end, a length extending from the third proximal end to the third distal end, and a tubular member body defining a first tubular member opening on the third proximal end, a second tubular member opening on the third distal end, and a tubular member lumen extending from the first tubular member opening to the second tubular member opening, the length of the tubular member being less than the length of the shaft;
- wherein the third distal end of the tubular member is disposed proximal to the first distal end of the elongate member,
- wherein the tubular member body defines a passageway that extends through the tubular member body and provides access to the tubular member lumen,
- wherein the tubular member has a frustoconical proximal portion that tapers from the third proximal end toward the third distal end;
- wherein the tubular member lumen has a frustoconical proximal portion that tapers from the third proximal end toward the third distal end;
- wherein the intermediate member body defines a first surface, a second surface, a frustoconical protuberance, and a support post, the first surface disposed on the second proximal end and opposably facing the second surface, the frustoconical protuberance extending distally from the second surface and tapering from the second surface toward the second distal end, the support post extending distally from the frustoconical protuberance to a support post end;
- wherein the frustoconical protuberance is disposed within the frustoconical proximal portion of the tubular member lumen; and
- wherein the support post is disposed within the passageway defined by the tubular member body.

3. A medical device for the treatment of a bodily passage, said medical device comprising:
- an elongate member having a proximal portion and a shaft extending distally from the proximal portion, the proximal portion having a first outside diameter, the shaft having a first proximal end attached to the proximal portion, a tapered first distal end, and a length extending from the first proximal end to the first distal end, the shaft having a second outside diameter that is less than the first outside diameter;
- an intermediate member releasably disposed on the shaft and having a second proximal end, a second distal end, an intermediate member body, and a third outside diameter that is greater than the first outside diameter of the proximal portion, the intermediate member body defining a first intermediate member opening, a second intermediate member opening, an intermediate member lumen, a first surface, a second surface, a frustoconical protuberance, and a support post, the first intermediate member opening defined on the second proximal end, the second intermediate member opening defined on the second distal end, the intermediate member lumen extending from the first intermediate member opening to the second intermediate member opening, the intermediate member lumen having an inside diameter that is less than the first outside diameter of the proximal portion, the first surface disposed on the second proximal end and opposably facing the second surface, the frustoconical protuberance extending distally from the second surface and tapering from the second surface toward the second distal end, the support post extending distally from the frustoconical protuberance to a support post end; and
- a tubular member releasably disposed on the shaft distal to the intermediate member, the tubular member separable from the intermediate member and having a third proximal end, a tapered third distal end, a length extending from the third proximal end to the third distal end, a frustoconical proximal portion that tapers from the third proximal end toward the third distal end, and a tubular member body defining a first tubular member opening on the third proximal end, a second tubular member opening on the third distal end, a tubular member lumen extending from the first tubular member opening to the second tubular member opening, and a passageway extending through the frustoconical proximal portion and providing access to the tubular member lumen, the tubular member lumen having a frustoconical proximal portion that tapers from the third proximal end toward the third distal end, the length of the tubular member being less than the length of the shaft;
- wherein the third distal end of the tubular member is disposed proximal to the first distal end of the elongate member;
- wherein the frustoconical protuberance is disposed within the frustoconical proximal portion of the tubular member lumen; and
- wherein the support post is disposed within the passageway defined by the tubular member body.

* * * * *